United States Patent [19]
Piwinski et al.

[11] Patent Number: 5,438,062
[45] Date of Patent: * Aug. 1, 1995

[54] BENZO(5,6)CYCLOHEPTAPYRIDINES, COMPOSITIONS AND METHODS OF USE

[75] Inventors: John J. Piwinski, Parsippany; Ashit K. Ganguly, Upper Montclair; Michael J. Green, Skillman; Frank J. Villani, Fairfield; Jesse Wong, Union, all of N.J.

[73] Assignee: Schering Corporation, Kenilworth, N.J.

[*] Notice: The portion of the term of this patent subsequent to Feb. 18, 2009 has been disclaimed.

[21] Appl. No.: 950,986

[22] Filed: Sep. 23, 1992

Related U.S. Application Data

[60] Continuation of Ser. No. 816,777, Jan. 2, 1992, abandoned, which is a division of Ser. No. 345,604, May 1, 1989, Pat. No. 5,089,496, which is a continuation-in-part of Ser. No. 181,860, Apr. 15, 1988, abandoned, which is a continuation-in-part of Ser. No. 925,342, Oct. 31, 1986, Pat. No. 4,826,853.

Foreign Application Priority Data

Oct. 29, 1987 [EP] European Pat. Off. .......... 87115890

[51] Int. Cl.$^6$ ................. C07D 221/06; C07D 401/14; A61K 31/44; A61K 31/495
[52] U.S. Cl. .................... 514/290; 514/255; 544/361; 546/286; 546/323; 546/93
[58] Field of Search .................. 546/93, 79; 514/290; 544/361, 255

[56] References Cited

U.S. PATENT DOCUMENTS

| | | | |
|---|---|---|---|
| 3,326,924 | 6/1967 | Villani | 546/93 |
| 3,357,986 | 12/1967 | Villani | 546/93 |
| 3,409,621 | 11/1968 | Villani | 544/361 |
| 3,419,565 | 12/1968 | Villani | 546/93 |
| 3,682,930 | 8/1972 | Bourquin et al. | 546/202 |
| 3,717,647 | 2/1973 | Villani | 546/315 |
| 3,749,786 | 7/1973 | Bourquin et al. | 514/324 |
| 3,960,894 | 6/1976 | Bourquin et al. | 549/44 |
| 4,034,095 | 7/1977 | Bastian | 514/290 |
| 4,128,549 | 12/1978 | Bourquin et al. | 546/202 |
| 4,282,233 | 8/1981 | Villani | 546/93 X |
| 4,355,036 | 10/1982 | Villani | 546/80 X |
| 4,356,184 | 10/1982 | Deason et al. | 514/324 |
| 4,609,664 | 9/1986 | Hasspacher | 514/324 |
| 4,616,023 | 10/1986 | Remy et al. | 514/323 |
| 4,659,716 | 4/1987 | Villani et al. | 514/290 |
| 4,826,853 | 5/1989 | Piwinski et al. | 514/290 |
| 5,089,496 | 2/1992 | Piwinski et al. | 514/253 |
| 5,151,423 | 9/1992 | Piwinski et al. | 514/254 |

OTHER PUBLICATIONS

Villani et al. "Derivatives of 10, 11-Dihydro-5-H-dibenzo [a,d] cycloheptene ..." J. Med. Chem. vol. 15, No. 7, pp. 750-754 (1972).

Villani et al., "N-substituted 11-(4-piperidylidene)-5,6 dihydro-11H-benzo(5,6)cyclohepta(1,2-b)pyridines", Arzneimittel-Forschung/Drug Research, vol. 36 (II), No. 9, 1311-1314 (1986).

Maurer et al., J. Chromatogr., 382, (1986), 147-165.
Maurer et al., J. Chromatogr., 430, (1988), 31-41.
Maurer et al., J. Clin. Chem. Clin. Biochem., 25, No. 9 620, 1987 with translation.

*Primary Examiner*—Alan L. Rotman
*Attorney, Agent, or Firm*—Henry C. Jeanette; James R. Nelson

[57] ABSTRACT

Derivatives of benzo[5,6]cyclohepta pyridine, and pharmaceutically acceptable salts and solvates thereof are disclosed, which possess anti-allergic and anti-inflammatory activity. Methods for preparing and using the compounds are also described.

8 Claims, No Drawings

BENZO(5,6)CYCLOHEPTAPYRIDINES, COMPOSITIONS AND METHODS OF USE

The present application is a continuation of U.S. application Ser. No. 07/816,777 now abandoned, filed Jan. 2, 1992, which is a division of U.S. application Ser. No. 345,604, filed May 1, 1989 (now U.S. Pat. No. 5,089,496), which is a continuation-in-part of U.S. application Ser. No. 181,860, filed Apr. 15, 1988, now abandoned which in turn is a continuation-in-part of U.S. application Ser. No. 925,342, filed Oct. 31, 1986 (now U.S. Pat. No. 4,826,853); and the benefits of these application is claimed under 35 U.S.C. 120.

The present invention relates to benzo[5,6]cycloheptapyridines and to pharmaceutical compositions and methods of using such compounds.

U.S. Pat. Nos. 3,326,924, 3,717,647 and 4,282,233, European published Application No. 0042544 and Villani et al., *Journal of Medicinal Chemistry*, Vol. 15, No. 7, pp 750–754 (1972) and *Arzn. Forch* 36 1311–1314 (1986) describe certain 11-(4-piperidylidene)-5H-benzo[5,6]cyclohepta [1,2-b]pyridines as antihistamines. U.S. Pat. No. 4,355,036 describes certain N-substituted piperidylidene compounds.

The invention in its chemical compound aspect is a compound having the structural formula I:

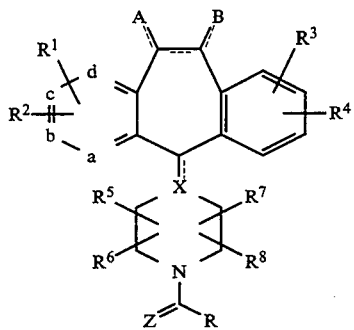

or a pharmaceutically acceptable salt or solvate thereof, wherein:

one of a, b, c and d represents N or $NR^9$ where $R^9$ is $O^-$, $-CH_3$ or $-(CH_2)_nCO_2H$ where n is 1 to 3, and the remaining a, b, c and d groups are CH, which remaining a, b, c and d groups optionally may be substituted with $R^1$ or $R^2$;

$R^1$ and $R^2$ may be the same or different and each independently represents halo, $-CF_3$, $-OR^{10}$, $-COR^{10}$, $-SR^{10}$, $-N(R^{10})_2$, $-NO_2$, $-OC(O)R^{10}$, $-CO_2R^{10}$, $-OCO_2R^{11}$, alkynyl, alkenyl or alkyl, which alkyl or alkenyl group may be substituted with halo, $-OR^{11}$ or $-CO_2$;

$R^3$ and $R^4$ may be the same or different and each independently represents H, any of the substituents of $R^1$ and $R^2R^3R^4$, or and together may represent a saturated or unsaturated $C_5$–$C_7$ ring fused to the benzene ring;

$R^5$, $R^6$, $R^7$ and $R^8$ each independently represent H, $-CF_3$, $-COR^{10}$, $-CO_2R^{10}$, alkyl or aryl, which alkyl or aryl may be substituted with $-OR^{10}$, $-SR^{10}$, $-N(R^{10})_2$, $-NO_2$, $COR^{10}$, $OCOR^{10}$, $OCO_2R^{11}$, $CO_2R^{10}$, $OPO_3R^{10}$ or one of $R^5$, $R^6$, $R^7$, and $R^8$ may be taken in combination with R as defined below to represent $-(CH_2)_r-$ where r is 1 to 4 which may be substituted with lower alkyl, lower alkoxy, $-CF_3$ or aryl or $R^5$ may be combined with $R^6$ to represent $=O$ or $=S$, and $R^7$ may be combined with $R^8$ to represent $=O$ or $=S$;

$R^{10}$ represents H, alkyl or aryl;
$R^{11}$ represents alkyl or aryl;
X represents N or C;

when X represents C, an optional double bond to carbon atom 11 may be present;

the dotted line between carbon atoms 5 and 6 represents an optional double bond, such that when a double bond is present, A and B independently represent H, $-R^{10}$, $-OR^{10}$ or $-OC(O)R^{10}$, and when no double bond is present between carbon atoms 5 and 6, A and B each independently represent $H_2$, $-(OR^{10})_2$, H and halo, dihalo, alkyl and H, (alkyl)$_2$, $-H$ and $-OC(O)R^{10}$, H and $-OR^{10}$, $=O$, aryl and H, $=NOR^{10}$ or $-O-(CH_2)_p-O-$ where p is 2, 3 or 4 and $R^{10}$ is as previously defined;

Z represents O, S, $=NR^{13}$ or $H_2$ with $R^{13}$ representing $R^{10}$ or $-CN$ such that (a) when Z is O or $NR^{13}$, R may be taken in combination with $R^5$, $R^6$, $R^7$ or $R^8$ as defined above, or R represents H, aryl, alkyl, $-SR^{11}$, $-N(R^{10})_2$, cycloalkyl, alkenyl, alkynyl or $-D$ wherein $-D$ represents heterocycloalkyl,

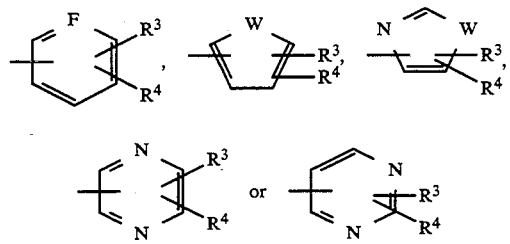

wherein $R^3$ and $R^4$ are as previously defined and W is O, S or $NR^{10}$ wherein $R^{10}$ is as defined above, said cycloalkyl, alkyl, alkenyl and alkynyl being optionally substituted with from 1–3 groups selected from halo, $-CON(R^{10})_2$, aryl, $-CO_2R^{10}$, $-OR^{12}$, $-SR^{12}$, $-N(R^{10})_2$, $-N(R^{10})CO_2R^{10}$, $-COR^{12}$, $-NO_2$ or D, wherein $-D$ and $R^{10}$ are as defined above and $R^{12}$ represents $R^{10}$, $-(CH_2)_mOR^{10}$ or $-(CH_2)_qCO_2R^{10}$ wherein $R^{10}$ is as previously defined, m is 1 to 4 and q is 0 to 4, said alkenyl and alkynyl R groups not containing $-OH$, $-SH$ or $-N(R^{10})_2$ on a carbon containing a double or triple bond respectively;

(b) when Z represents S, R represents in addition to those R groups above, aryloxy or alkoxy; and (c) when Z represents $H_2$, R represents $-COOR^{10}$, $-E-COOR^{10}$ or $-E-OR^{12}$ where E is alkanediyl which may be substituted with aryl $-OR^{10}$, $-SR^{10}$, $-N(R^{10})_2$ or $-D$ where D, $R^{10}$ and $R^{12}$ are as previously defined.

In a preferred embodiment of the invention, Z represents O or S, and R represents alkyl, cycloalkyl, alkenyl, aryl or alkyl substituted with $-OR^{12}$, $-SR^{12}$, $-N(R^{10})_2$ or $-COR^{12}$. More preferably, when Z represents O or S, R represents alkyl having from 1 to 3 carbon atoms, or alkyl of from 1 to 3 carbon atoms substituted with $-OR^{12}$, $-SR^{12}$, $-N(R^{10})_2$, or $COR^{12}$. Preferably one or both of $R^3$ and $R^4$ is halo, e.g. chloro or fluoro. The most preferred value of $R^3$ and/or $R^4$ is a halogen located at carbon atom 8 and/or 9, as shown in the following numbered ring structure:

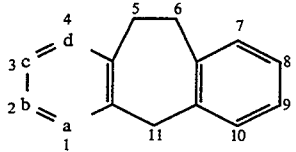

The nitrogen preferably is located at position "a". $R^5$, $R^6$, $R^7$, $R^8$, A and B preferably are H. X preferably is a single or double bonded carbon. The bond between positions 5 and 6 preferably is a single bond. The bond between the piperidyl ring and the cycloheptyl ring preferably is a double bond.

Preferably when Z is $H_2$, R is —E—COOR$^{10}$ or —E—OR$^{12}$.

Compounds of the invention include:

11-(1-acetyl-4-piperidylidene)-6,11-dihydro-5H-benzo[5,6]cyclohepta[1,2-b]pyridine;

11-(1-methoxyacetyl-4-piperidylidene)-6,11-dihydro-5H-benzo[5,6]cyclohepta[1,2-b]pyridine;

11-(1-benzoyl-4-piperidylidene)-6,11-dihydro-5H-benzo[5,6]cyclohepta[1,2-b]pyridine;

11-[1-(3-chlorophenylacetyl)-4-piperidylidene]-6,11-dihydro-5H-benzo[5,6]cyclohepta[1,2-b]pyridine;

11-[1-(3,4-dimethoxybenzoyl)-4-piperidylidene]-6,11-dihydro-5H-benzo[5,6]cyclohepta[1,2-b]pyridine;

8-chloro-11-(1-acetyl-4-piperidylidene)-6,11-dihydro-5H-benzo[5,6]cyclohepta[1,2-b]pyridine;

8-chloro-11-(1-propionyl-4-piperidylidene)-6,11-dihydro-5H-benzo[5,6]cyclohepta[1,2-b]pyridine;

8-chloro-11-(1-trimethylacetyl-4-piperidylidene)-6,11-dihydro-5H-benzo[5,6]cyclohepta[1,2-b]pyridine;

8-chloro-11-[1-(t-butylacetyl)-4-piperidylidene]-6,11-dihydro-5H-benzo[5,6]cyclohepta[1,2-b]pyridine;

8-chloro-11-(1-methoxyacetyl-4-piperidylidene)-6,11-dihydro-5H-benzo[5,6]cyclohepta[1,2-b]pyridine;

8-chloro-11-[1-(ethoxyacetyl)-4-piperidylidene]-6,11-dihydro-5H-benzo[5,6]cyclohepta[1,2-b]pyridine;

8-chloro-11-[1-(2-hydroxypropioyl)-4-piperidylidene]-6,11-dihydro-5H-benzo[5,6]cyclohepta[1,2-b]pyridine;

9-chloro-11-(1-methoxyacetyl-4-piperidylidene)-6,11-dihydro-5H-benzo[5,6]cyclohepta[1,2-b]pyridine;

8-chloro-11-[1-(2-methoxypropioyl)-4piperidylidene]-6,11-dihydro-5H-benzo[5,6]cyclohepta[1,2-b]pyridine;

8-chloro-11-[1-(2-oxopropioyl)-4-piperidylidene]-6,11-dihydro-5H-benzo[5,6]-cyclohepta[1,2-b]pyridine;

8-chloro-11-[1-(1-ethoxycarbonylmethyl)-4-piperidylidene]6,11-dihydro-5H-benzo[5,6]cyclohepta[1,2-b]pyridine;

8-chloro-11-[1-(t-butoxycarbonylaminoacetyl)-4-piperidylidene]-6,11-dihydro-5H-benzo[5,6]cyclohepta[1,2-b]pyridine;

8-chloro-11-(1-trifluoroacetyl-4-piperidylidene)-6,11-dihydro-5H-benzo[5,6]cyclohepta[1,2-b]pyridine;

8-chloro-11-(1-benzoyl-4-piperidylidene)-6,11-dihydro-5H-benzo[5,6]cyclohepta[1,2-b]pyridine;

8-chloro-11-[1-(3,4,5-trimethoxybenzoyl)-4-piperidylidene]-6,11-dihydro-5H-benzo[5,6]cyclohepta[1,2-b]pyridine;

8-fluoro-11-(1-acetyl-4-piperidylidene)-6,11-dihydro-5H-benzo[5,6]cyclohepta[1,2-b]pyridine;

8-fluoro-11-(1-n-butyryl-4-piperidylidene)-6,11-dihydro-5H-benzo[5,6]cyclohepta[1,2-b]pyridine;

8-fluoro-11-(1-methoxyacetyl-4-piperidylidene)-6,11-dihydro-5H-benzo[5,6]cyclohepta[1,2-b]pyridine;

9-fluoro-11-(1-acetyl-4-piperidylidene)-6,11-dihydro-5H-benzo[5,6]cyclohepta[1,2-b]pyridine;

9-fluoro-11-(1-methoxyacetyl-4-piperidylidene)-6,11-dihydro-5H-benzo[5,6]cyclohepta[1,2-b]pyridine;

3-methyl-8-chloro-11-(1-acetyl-4-piperidylidene)-6,11-dihydro-5H-benzo[5,6]cyclohepta[1,2-b]pyridine;

8,9-difluoro-11-(1-methoxyacetyl-4-piperidylidene)-6,11-dihydro-5H-benzo[5,6]cyclohepta[1,2-b]pyridine;

8-methyl-11-(1-methoxyacetyl-4-piperidylidene)-6,11-dihydro-5H-benzo[5,6]cyclohepta[1,2-b]pyridine;

8-chloro-11-(1-cyclopropylcarbonyl-4-piperidylidene)-6,11-dihydro-5H-benzo[5,6]cyclohepta[1,2-b]pyridine;

8-chloro-11-(1-n-butyryl-4-piperidylidene)-6,11-dihydro-5H-benzo[5,6]cyclohepta[1,2-b]pyridine;

8-methoxy-11-(1-acetyl-4-piperidylidene)-6,11-dihydro-5H-benzo[5,6]cyclohepta[1,2-b]pyridine;

9-chloro-11-(1-acetyl-4-piperidylidene)-6,11-dihydro-5H-benzo[5,6]cyclohepta[1,2-b]pyridine;

8,9-difluoro-11-(1-acetyl-4-piperidylidene)-6,11-dihydro-5H-benzo[5,6]cyclohepta[1,2-b]pyridine;

8-methyl-11-(1-acetyl-4-piperidylidene)-6,11-dihydro-5H-benzo[5,6]cyclohepta[1,2-b]pyridine;

8,9-dichloro-11-(1-acetyl-4-piperidylidene)-6,11-dihydro-5H-benzo[5,6]cyclohepta[1,2-b]pyridine;

8-chloro-11-[1-(2-(2-hydroxyethoxy)ethyl)-4piperidylidene]-6,11-dihydro-5H-benzo[5,6]cyclohepta[1,2-b]pyridine;

8-chloro-11-[1-[4-(4-t-butylphenyl)-4-hydroxybutyl]-4-piperidylidene]-6,11-dihydro-5H-benzo[5,6]cyclohepta[1,2-b]pyridine;

8-chloro-11-(1-ethoxydicarbonyl-4-piperidylidene)-6,11-dihydro-5H-benzo[5,6]cyclohepta[1,2-b]pyridine;

8-chloro-11-(1-aminoacetyl-4-piperidylidene)-6,11-dihydro-5H-benzo[5,6]cyclohepta[1,2-b]pyridine;

8-chloro-11-(1-formyl-4-piperidylidene)-6,11-dihydro-5H-benzo[5,6]cyclohepta[1,2-b]pyridine;

8-chloro-11-(1-thiobenzoyl-4-piperidylidene)-6,11-dihydro-5H-benzo[5,6]cyclohepta[1,2-b]pyridine;

8-chloro-11-[1-thioethoxycarbonyl-4-piperidylidene]-6,11-dihydro-5H-benzo[5,6]cyclohepta[1,2-b]pyridine;

8-chloro-11-[1-thioacetyl-4-piperidylidene]-6,11-dihydro-5H-benzo[5,6]cyclohepta[1,2-b]pyridine;

8-bromo-11-[1-acetyl-4-piperidylidene]-6,11-dihydro-5H-benzo[5,6]cyclohepta[1,2-b]pyridine;

8-chloro-11-(1-acetyl-4-piperidylidene)-6,11-dihydro-5H-benzo[5,6]cyclohepta[1,2-b]pyridine N-oxide;

8-chloro-11-(1-acetyl-4-piperidylidene)-11H-benzo[5,6]cyclohepta[1,2-b]pyridine;

8-chloro-11-(1-acetyl-4-piperazinyl)-6,11-dihydro-5H-benzo[5,6]cyclohepta[1,2-b]pyridine;

8-chloro-11-(1-methylaminocarbonyl-4-piperidylidene)-6,11-dihydro-5H-benzo[5,6]cyclohepta[1,2-b]pyridine;

13-(1-acetyl-4-piperidylidene)6,13-dihydro-5H-naphtho[2′,3′:5,6]cyclohepta[1,2-b]pyridine;

8-chloro-11-[1-acryloyl-4-piperidylidene]-6,11-dihydro-5H-benzo[5,6]cyclohepta[1,2-b]pyridine;

8-chloro-11-[1-(2-methoxy-2-methylpropionyl)-4-piperidylidene]-6,11-dihydro-5H-benzo[5,6]cyclohepta[1,2-b]pyridine;

1-methyl-8-chloro-11-(1-acetyl-4-piperidylidene)-6,11-dihydro-5H-benzo[5,6]cyclohepta[1,2-b]pyridinium iodide;

8-chloro-11-[1-acetyl-4-piperidinyl]-11H-benzo[5,6-]cyclohepta[1,2-b]pyridine;

5-hydroxy-8-chloro-11-(1-acetyl-4-piperidylidene)-6,11-dihydro-5H-benzo[5,6]cyclohepta[1,2-b]pyridine;

8-chloro-11-[1-dichloroacetyl-4-piperidylidene]-6,11-dihydro-5H-benzo[5,6]cyclohepta[1,2-b]pyridine;

5-methyl-8-chloro-11-[1-acetyl-4-piperidylidene]-5H-benzo[5,6]cyclohepta[1,2-b]pyridine;

3-methyl-8-chloro-11-[1-acetyl-4-piperidylidene]-5H-benzo[5,6]cyclohepta[1,2-b]pyridine;

8-chloro-11-[1-acetyl-4-piperidylidene]-6,11-dihydro-5H-benzo[5,6]cyclohepta[1,2-b]pyridin-5-one;

5-methyl-8-chloro-(1-acetyl-4-piperazinyl)-6,11-dihydro-5H-benzo[5,6]cyclohepta[1,2-b]pyridine;

8-chloro-11-[1-acetyl-2-methyl-4-piperazinyl]-6,11-dihydro-5H-benzo[5,6]cyclohepta[1,2-b]pyridine;

8-chloro-11-[1-acetyl-(E)-2,6-dimethyl-4-piperidylidene]-6,11-dihydro-5H-benzo[5,6]cyclohepta[1,2-b]pyridine;

8-chloro-11-[1-acetyl-(Z)-2,6-dimethyl-4-piperidylidene]-6,11-dihydro-5H-benzo[5,6]cyclohepta[1,2-b]pyridine;

8-chloro-11-[1-acetyl-2,6-dimethyl-4-piperazinyl]-6,11-dihydro-5H-benzo[5,6]cyclohepta[1,2-b]pyridine;

8-chloro-11-(1-methoxyacetyl-4-piperazinyl)-6,11-dihydro-5H-benzo[5,6]cyclohepta[1,2-b]pyridine;

8,9-difluoro-11-(1-acetyl-4-piperidylidene)-6,11-dihydro-5H-benzo[5,6]cyclohepta[1,2-b]pyridine-N-oxide;

8-chloro-11-(1-formyl-4-piperazinyl)-6,11-dihydro-5H-benzo[5,6]cyclohepta[1,2-b]pyridine;

8-chloro-11-(1-acetyl-4-piperidyl)-6,11-dihydro-5H-benzo[5,6]cyclohepta[1,2-c]pyridine;

2-[8-chloro-5,6-dihydro-11H-benzo[5,6]cyclohepta[1,2-b]pyridin-11-yl]hexahydropyrrolo[1,2-a]pyrazin-6(2H)-one;

11-[1-(aminocarbonyl)-4-piperidylidene-6,11-dihydro-5H-benzo[5,6]cyclohepta[1,2-c]pyridine; and 3,8-dichloro-11-(1-acetyl-4-piperidylidene)-6,11-dihydro-5H-benzo[5,6]cyclohepta[1,2-b]pyridine.

Particularly preferred compounds include:

8-chloro-11-(1-acetyl-4-piperidylidene)-6,11-dihydro-5H-benzo[5,6]cyclohepta[1,2-b]pyridine;

8-chloro-11-(1-methoxyacetyl-4-piperidylidene)-6,11-dihydro-5H-benzo[5,6]cyclohepta[1,2-b]pyridine;

8-chloro-11-(1-propionyl-4-piperidylidene)-6,11-dihydro-5H-benzo[5,6]cyclohepta[1,2-b]pyridine;

8-fluoro-11-(1-acetyl-4-piperidylidene)-6,11-dihydro-5H-benzo[5,6]cyclohepta[1,2-b]pyridine;

9-fluoro-11-(1-acetyl-4-piperidylidene)-6,11-dihydro-5H-benzo[5,6]cyclohepta[1,2-b]pyridine;

8-bromo-11-[1-acetyl-4-piperidylidene]-6,11-dihydro-5H-benzo[5,6]cyclohepta[1,2-b]pyridine;

8,9-difluoro-11-(1-acetyl-4-piperidylidene)-6,11-dihydro-5H-benzo[5,6]cyclohepta[1,2-b]pyridine;

11-(1-acetyl-4-piperidyl)-6,11-dihydro-5H-benzo[5,6-]cyclohepta[1,2-b]pyridine;

3,8-dichloro-11-(1-acetyl-4-piperidylidene)-6,11-dihydro5H-benzo[5,6]cyclohepta[1,2-b]pyridine;

3-methyl-8-chloro-11-(1-acetyl-4-piperidylidene)-6,11-dihydro-5H-benzo[5,6]cyclohepta[1,2-b]pyridine;

8-chloro-11-(1-acetyl-4-piperazinyl)-6,11-dihydro-5H-benzo[5,6]cyclohepta[1,2-b]pyridine; and 8-chloro-11-(1-acetyl-4-piperidylidene)-6,11-dihydro-5H-benzo[5,6]cyclohepta[1,2-b]pyridine N-oxide.

The invention also is directed at a process for producing a compound having structural formula I wherein the substituents are as previously defined by:

a) reacting a compound of formula II with a compound of formula III, wherein L represents a suitable leaving group

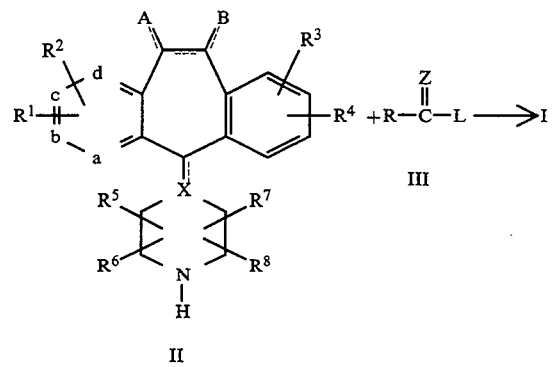

b) direct conversion of an N-alkyl compound of formula V with a compound of formula III

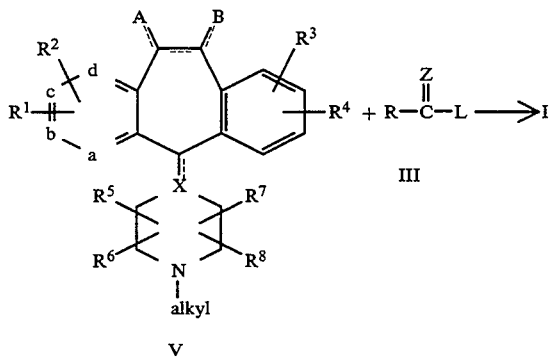

or, c) cyclization of a compound of formula XII

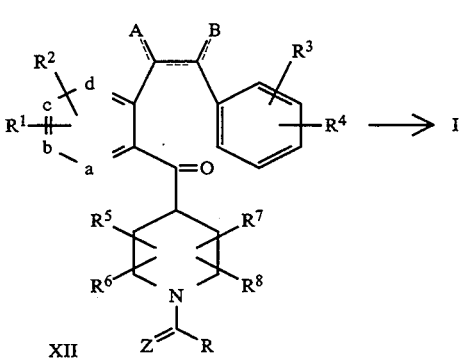

The invention also is directed at a compound of the formula XII

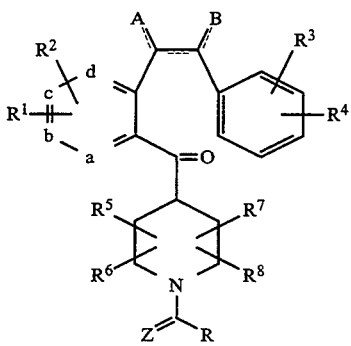

XII wherein the substituents have the same definitions as in formula I.

The invention also encompasses a pharmaceutical composition which comprises a compound of formula I as defined above in combination with a pharmaceutically acceptable carrier.

The invention further encompasses a method of treating allergy or inflammation in a mammal, comprising administering a compound of formula I to said mammal in an amount effective to treat allergy or inflammation, respectively.

The invention also comprises a method for making a pharmaceutical composition comprising mixing a compound of formula I with a pharmaceutically acceptable carrier.

As used herein, the following terms are used as defined below unless otherwise indicated:

- alkyl—(including the alkyl portions of alkoxy, alkylamino and dialkylamino)—represents straight and branched carbon chains and contains from one to twenty carbon atoms, preferably one to six carbon atoms;
- alkanediyl—represents a divalent, straight or branched hydrocarbon chain having from 1 to 20 carbon atoms, preferably 1 to 6 carbon atoms, the two available bonds being from the same or different carbon atoms thereof, e.g., methylene, ethylene, ethylidene, —CH$_2$CH$_2$CH$_2$—, —CH$_2$CHCH$_3$, —CHCH$_2$CH$_3$, etc.
- cycloalkyl—represents saturated carbocyclic rings branched or unbranched of from 3 to 20 carbon atoms, preferably 3 to 7 carbon atoms;
- heterocycloalkyl—represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —NR$^{10}$— (suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);
- alkenyl—represents straight and branched carbon chains having at least one carbon to carbon double bond and containing from 2 to 12 carbon atoms, preferably from 3 to 6 carbon atoms;
- alkynyl—represents straight and branched carbon chains having at least one carbon to carbon triple bond and containing from 2 to 12 carbon atoms, preferably from 2 to 6 carbon atoms;
- aryl (including the aryl portion of aryloxy)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted with one or more of halo, alkyl, hydroxy, alkoxy, phenoxy, CF$_3$, amino, alkylamino, dialkylamino, —COOR$^{10}$ or —NO$_2$; and
- halo—represents fluoro, chloro, bromo and iodo.

Certain compounds of the invention may exist in different isomeric as well as conformational forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

As noted above, the pyridine and benzene ring structures of formula I may contain one or more substituents R$^1$, R$^2$, R$^3$ and R$^4$. Similarly, the heterocyclic ring D may contain one or more of R$^3$ and R$^4$. In compounds where there is more than one such substituent, they may be the same or different. Thus compounds having combinations of such substituents are within the scope of the invention. Also, the lines drawn into the rings from the R$^1$, R$^2$, R$^3$ and R$^4$ groups indicate that such groups may be attached at any of the available positions. For example, the R$^1$ and R$^2$ groups may be attached at the 1, 2, 3 or 4 positions while the R$^3$ and R$^4$ groups may be attached at any of the 7, 8, 9 or 10 positions.

R$^5$, R$^6$, R$^7$ and R$^8$ are attached to the piperidylidene or piperazine ring. As such they may be the same or different The variables R$^5$ and R$^6$, in addition to representing H, may represent variables attached to the same or different carbon atoms in said ring. For example, when R$^5$ and R$^6$ are combined to represent =O or =S, they are attached to the same carbon atom. Similarly, R$^7$ and R$^8$ may be attached to the same carbon atom, such as when R$^7$ and R$^8$ together represent =O or =S. Also, one of R$^5$, R$^6$, R$^7$ and R$^8$ may be taken in combination with R to represent an alkylene chain, —(CH$_2$)$_r$—, where r is 1 to 4, thereby forming a fused ring which contains a nitrogen.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts and quaternary ammonium salts. For example, the pyrido- or pyrazino- nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g., by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

All such acid, base and quaternary salts are intended to be pharmaceutically acceptable salts within the scope of the invention and all acid and base salts are considered equivalent to the free forms of the corresponding compounds for purposes of the invention.

The following processes may be employed to produce compounds of general structural formula I.

A. A compound of general formula II may be reacted with compound III in the presence of base to produce compounds of general structural formula I.

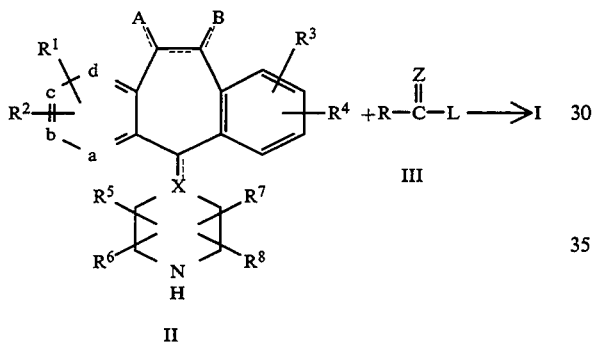

Representative examples of appropriate bases are pyridine and triethylamine. L designates a suitable leaving group. For example, if Z is 0 or S, a compound of compound III may be an acyl halide (e.g., L=halo) or acyl anhydride, (e.g., L is

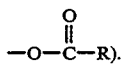

Alternatively, if the leaving group is hydroxy, a coupling reagent may be employed to form Compound I. Examples of coupling agents include N,N'-dicyclohexylcarbodiimide (DCC) and N,N'-carbonyldiimidazole (CDI). The leaving group may also be alkoxy, in which case the compounds of formula I may be produced by refluxing a compound of formula II with an excess of a compound of formula III.

If compound III is a compound R—CH$_2$—L, L can be any easily displaced group, such as halo, p-toluene sulfonyloxy, methyl sulfonyloxy, trifluoromethylsulfonyloxy and the like.

Compounds of general formula II may be prepared by cleaving the group COOR$^a$ from the corresponding carbamates IV, for example, via acid hydrolysis (e.g., HCl) or base hydrolysis (e.g., KOH):

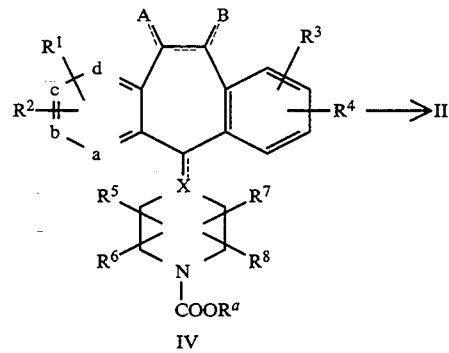

wherein R$^a$ is a group which does not prevent the cleavage reaction, e.g., R$^a$ is an optionally substituted alkyl such as ethyl.

Alternatively, depending upon the nature of R$^a$, as determined by one skilled in the art, Compound IV may be treated with an organometallic reagent (e.g., CH$_3$Li), a reductive reagent (e.g., Zn in acid), etc., to form compounds of formula II.

Compound IV may be prepared from the N-alkyl compound shown as formula V below, in the manner disclosed in U.S. Pat. Nos. 4,282,233 and 4,335,036.

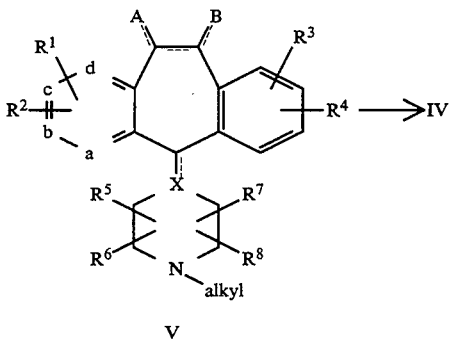

It also will be apparent to one skilled in the art that there are other methods for converting Compound V to Compound II. For example, treatment of Compound V with BrCN via von Braun reaction conditions would provide nitrile IVa. Subsequent hydrolysis of the nitrile under either aqueous basic or acidic conditions would produce Compound II. This method is preferable when there is substitution on the piperidine or piperazine ring.

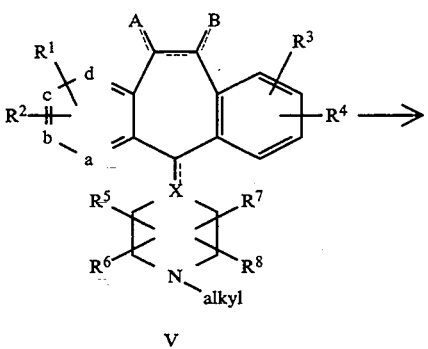

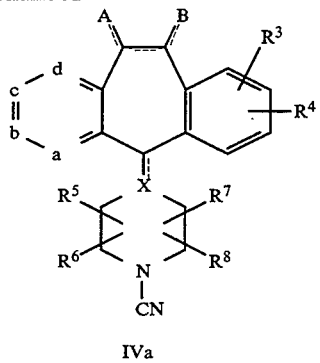

IVa

B. The compounds of formula I where Z is O or S may be made by an alternative process using direct conversion of the N-alkyl compound V with an appropriate compound of formula III such as an acyl halide or acyl anhydride. Preferably the reaction is run in the presence of an appropriate nucleophile (e.g. LiI, etc.) and solvent (e.g., toluene, dioxane or xylenes). An appropriate base, may be added, and heating may be required. Typically, a temperature ranging from 50°-150° C. (preferably 100°-120° C.) is utilized.

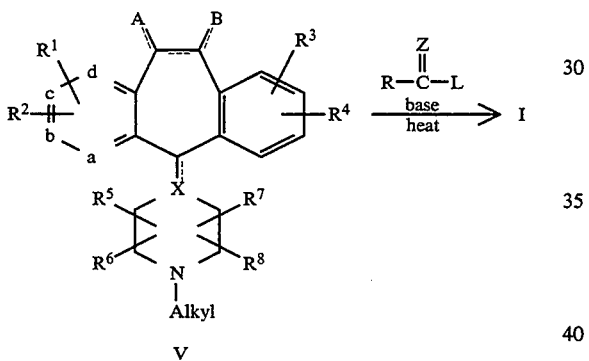

V

Compound V is prepared as described in part A above.

PREPARATION OF DOUBLE BOND COMPOUNDS

Compounds of the formula Ia, where X is a carbon atom having an exocyclic double bond to carbon 11, may be prepared from compound Va as described above. Compounds of formula Va may be produced by the methods disclosed generally in U.S. Pat. No. 3,326,924 or alternatively may be prepared by a ring closure reaction, wherein the desired cycloheptene ring is formed by treating compound VI with a super acid. Suitable super acids for this purpose include, for example, HF/BF$_3$, CF$_3$SO$_3$H (triflic acid), CH$_3$SO$_3$H/BF$_3$, etc. The reaction can be performed in the absence of, or with, an inert co-solvent such as CH$_2$Cl$_2$. The temperature and time of the reaction vary with the acid employed. For example, with HF/BF$_3$ as the super acid system the temperature may be controlled so as to minimize side reactions, such as HF addition to the exocyclic double bond. For this purpose, the temperature is generally in the range of from about +5° C. to −50° C. With CF$_3$SO$_3$H as the super acid system, the reaction may be run at elevated temperatures, e.g., from about 25° C. to about 150° C. and at lower temperatures but the reaction then takes longer to complete.

Generally the super acid is employed in excess, preferably in amounts of from about 1.5 to about 30 equivalents.

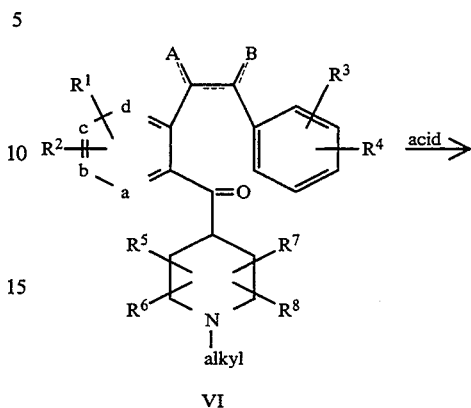

VI

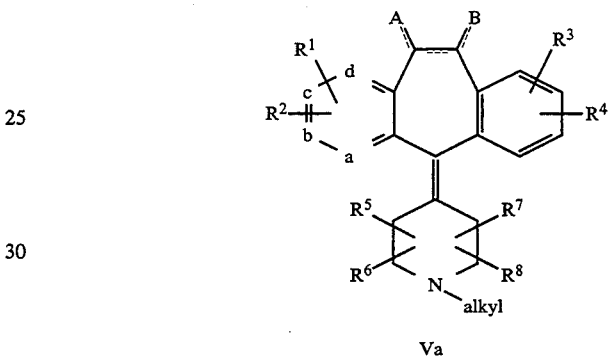

Va

A ketone compound of formula VI may be formed by hydrolysis of VII e.g., such as by reacting a Grignard intermediate of formula VII with an aqueous acid (e.g., aqueous HCl). I$^a$ in formula VII represents chloro, bromo or iodo.

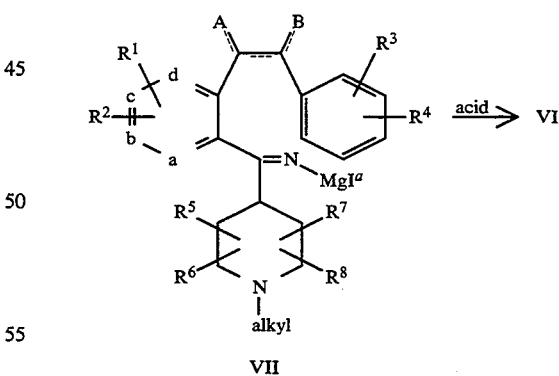

VII

The Grignard intermediate VII is formed by the reaction of the cyano compound VIII with an appropriate Grignard reagent IX prepared from 1-alkyl-4-halopiperidine. The reaction is generally performed in an inert solvent, such as ether, toluene, or tetrahydrofuran, under general Grignard conditions e.g., temperature of from about 0° C. to about 75° C. Alternatively, other organometallic derivatives of the 1-alkyl-4-halo piperidine can be employed.

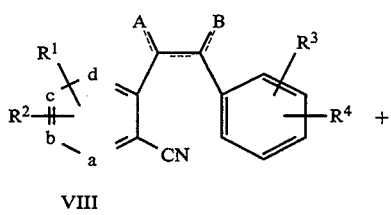

VIII

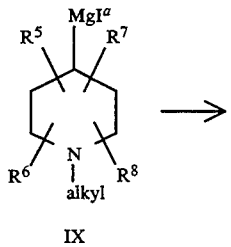

IX

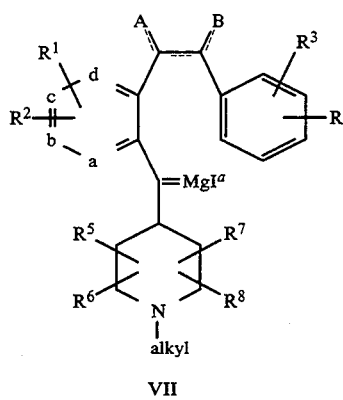

VII

The cyano compound of formula-VIII is produced by converting the tertiary butyl amide of formula X with a suitable dehydrating agent, such as $POCl_3$, $SOCl_2$, $P_2O_5$, toluene sulfonyl chloride in pyridine, oxalyl chloride in pyridine, etc. This reaction can be performed in the absence of or with a co-solvent, such as xylene.

The dehydrating agent such as $POCl_3$ is employed in equivalent amounts or greater and preferably in amounts of from about 2 to about 15 equivalents. Any suitable temperature and time can be employed for performing the reaction, but generally heat is added to accelerate the reaction. Preferably the reaction is performed at or near reflux.

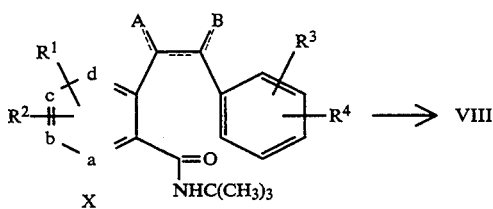

X

The tert-butylamide of formula X may be produced by reaction of a compound of formula XIa and XIb, in the presence of base, where G is chloro, bromo or iodo.

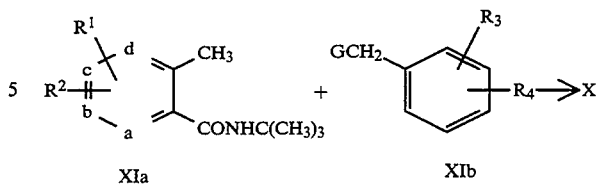

XIa    XIb

The compound of formula XIa may be formed by hydrolysis of the corresponding nitrile wherein the appropriate cyanomethyl pyridine, such as 2-cyano-3-pyridine, is reacted with a tertiary butyl compound in acid, such as concentrated sulfuric acid or concentrated sulfuric acid in glacial acetic acid. Suitable tertiary butyl compounds include, but are not limited to, t-butyl alcohol, t-butyl chloride, t-butyl bromide, t-butyl iodide, isobutylene or any other compound which under hydrolytic conditions forms t-butyl carboxamides with cyano compounds. The temperature of the reaction will vary depending upon the reactants, but generally the reaction is conducted in the range of from about 50° C. to about 100° C. with t-butyl alcohol. The reaction may be performed with inert solvents, but is usually run neat.

An alternative process for the formation of compounds having general structural formula Ia involves direct cyclization of the Compound XII as shown below.

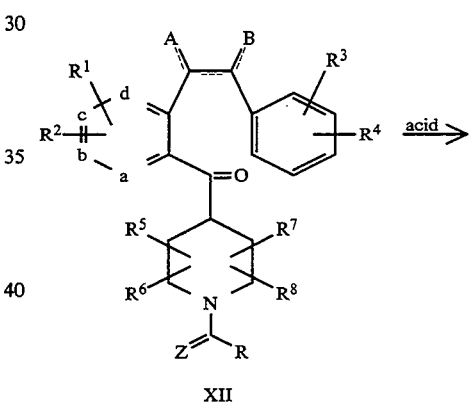

XII

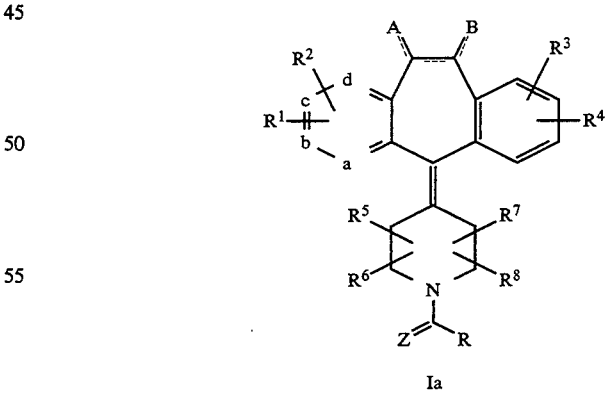

Ia

Cyclization to form the cycloheptene ring is accomplished with a strong acid (e.g., triflic, polyphosphoric, $HF/BF_3$), and may be performed in an inert solvent, such as ether, toluene or THF. The temperature and time may vary with the acid employed, as described in process A above.

Compounds of formula XII where $Z=O$ or S may be prepared by treating a compound of formula VI with an appropriate acyl halide or acyl anhydride of formula III. Most preferably this reaction is run in the presence of a good nucleophile, such as LiI, in the appropriate solvent, such as toluene, dioxane or xylene, and at a temperature ranging from 50°–150° C., preferably 100°–120° C.

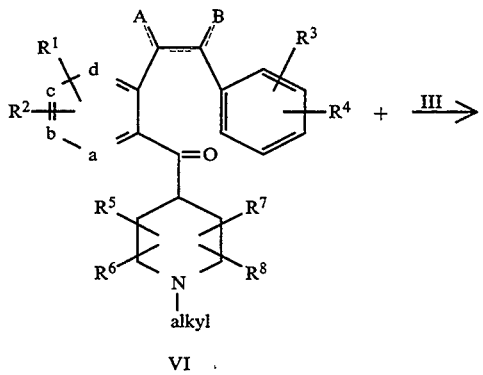

VI

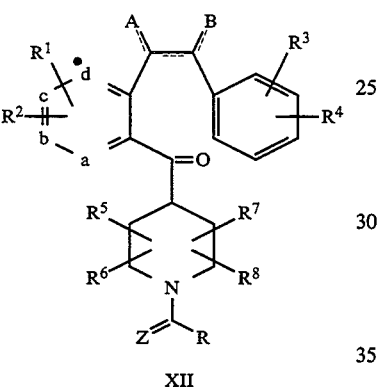

XII

A second method of preparing compounds of formula XII involves reacting an unsubstituted piperidylidene compound of formula XIV with the appropriate acyl halide or acyl anhydride of formula III in the presence of base, such as pyridine or triethylamine. Alternatively, if L=OH in compound III, then coupling of compound XIV with compound III may require use of a conventional coupling reagent, such as DCC or CDI. If compound III is of the formula RCH₂L, compounds of formula I where Z =H₂ will be produced. In such case, the leaving group can be any easily displaced group, such as halo, p-toluene sulfonyloxy, methyl sulfonyloxy, trifluoromethyl sulfonyloxy, etc.

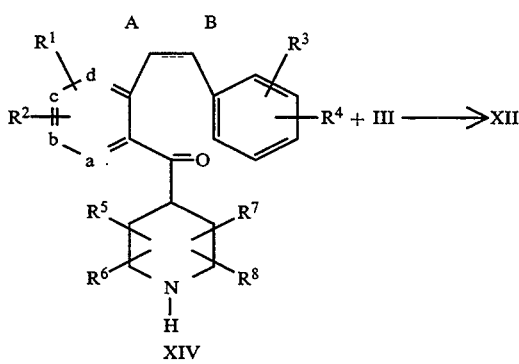

Compounds of formula XIV are produced from the corresponding carbamates of formula XV, via acid hydrolysis, using for example, aqueous hydrochloric acid, or base hydrolysis using for example, potassium hydroxide. Alternatively, some compounds can be prepared by treating the carbamate, formula XV, with an organometallic reagent, such as methyl lithium or a reductive reagent, such as zinc in acid, etc., depending upon the nature of the $R^a$ group. For example, if $R^a$ is a simple alkyl group, $CO_2R^a$ may be cleaved by alkaline hydrolysis at 100° C.

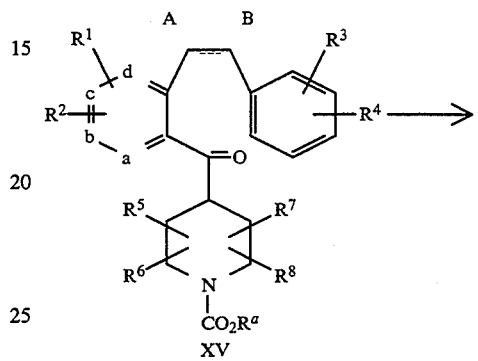

XV

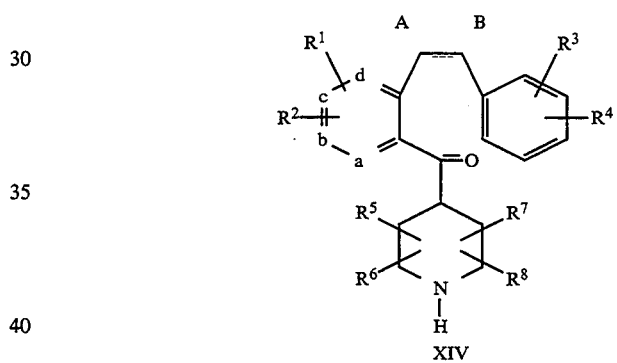

XIV

The carbamate compounds of formula XV may be prepared from the appropriate alkyl compound of formula VI by treatment with a chloroformate, preferably in an inert solvent, such as toluene, with warming to approximately 80° C. Other alternative methods are available for the conversion of XIII to XII as previously described (e.g. Von Braun reaction conditions).

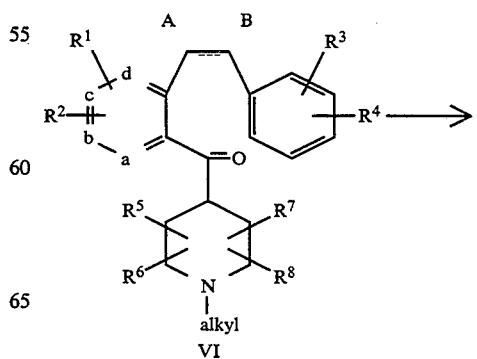

VI

-continued

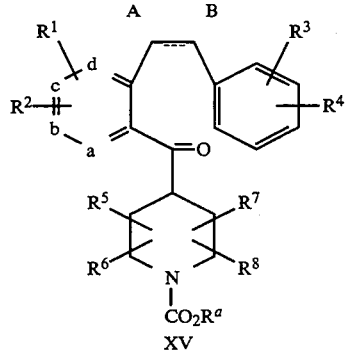
XV

Compounds of formula VI may be prepared as described in process A above.

PREPARATION OF PIPERAZINE ANALOGS

Compounds of the piperazine type Ib, where X is N in formula I, are best prepared via alkylation of the appropriately substituted piperazine Compound XVI with Compound XVII containing the appropriately substituted halide (such as Cl, Br, I) or other similar leaving group (tosyloxy or mesyloxy). The reaction usually is conducted in an inert solvent such as THF or toluene, optionally with a base such as triethylamine or potassium carbonate, typically at a temperature range of ambient to reflux to produce Compound XVIII.

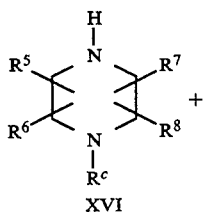
XVI

+

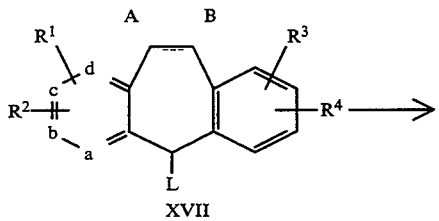
XVII

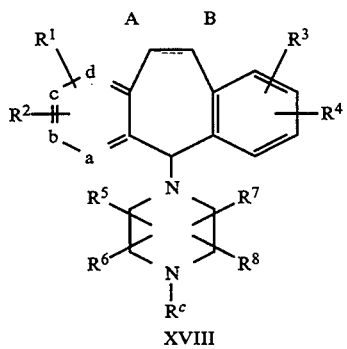
XVIII

In this reaction $R^c$ is H, $CO_2R^a$, C(Z)R or alkyl. The preparation of compound XVII where L is Cl is analogous to the procedure described in U.S. Pat. No. 3,409,621. When $R^c$ is C(Z)R, compounds of the invention are prepared. When $R^c$ is H, alkyl or $CO_2R^a$, the compounds are converted to compounds of the invention by processes previously described herein.

An alternative route for generating Compound XVIII is by reductive amination of the aza ketone XIX with the appropriately substituted piperazine XVI.

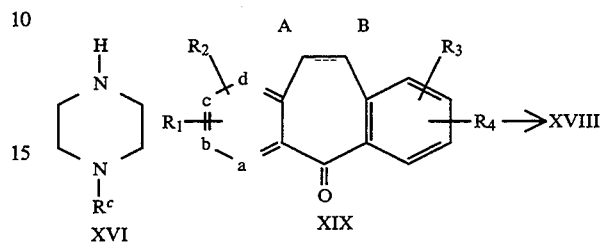
XVI    XIX

The reaction typically is carried out in a polar solvent, such as methanol or ethanol optionally in the presence of a dehydrating agent such as 3 Å molecular sieves. The intermediate Schiff base can be reduced to Compound XVIII by employing a variety of reducing agents such as $NaCNBH_3$ or catalytic hydrogenation, for example, hydrogen over Pd/C.

When $R^c$ is C(Z)R, these are the compounds of the present invention. When $R^c$ is H, $CO_2R^a$ or alkyl, these are converted to compounds of the invention as previously described.

PREPARATION OF SINGLE BOND COMPOUNDS

Compounds of the formula Ic, where X is a carbon atom having a single bond to carbon atom 11, may be prepared by the following methods.

A. Compounds of formula VI may be converted to the corresponding alcohol Compound XX by employing an appropriate reducing agent. The reduction can be accomplished with a variety of reducing agents (e.g. $NaBH_4$ or $LiAlH_4$) in an inert solvent such as THF or ether.

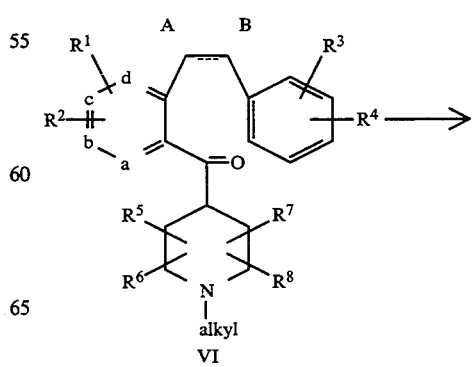
VI

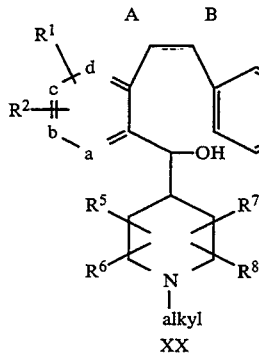

XX

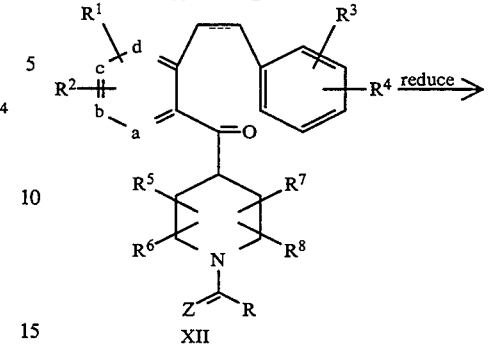

XII

Compound XX may be cyclized to Compound XXI via a variety of methods. For example, the cyclization may be conducted under conditions similar to those described for the cyclization of compound VI to compound V using, for example, PPA or triflic acid.

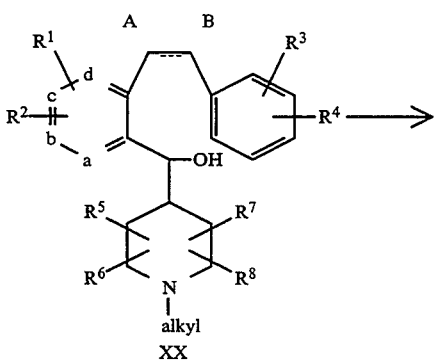

XX

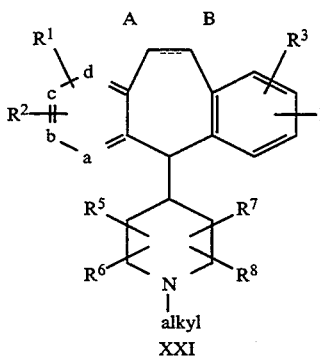

XXI

The alkyl substituted compound then may be converted to a compound of the present invention by previously described methods.

B. Alternatively, compounds of the invention can be prepared from compound XII by methods similar to those described with respect to the reduction of compound XII to compound XXII, and the cyclization of compound XXII to compound Ic.

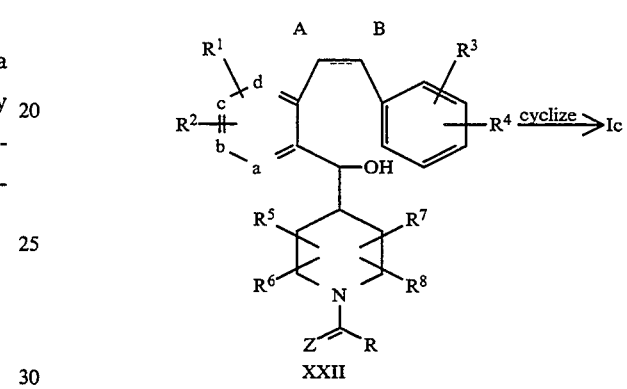

XXII

In formula XXIII the double bond can be catalytically hydrogenated to Compound XXIV by a variety of catalysts, such as Pt, Rh, Ru or Pd on various supports as described in U.S. Pat. Nos. 3,419,565; 3,326,924; and 3,357,986.

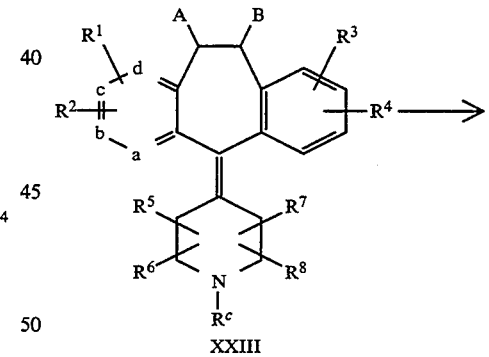

XXIII

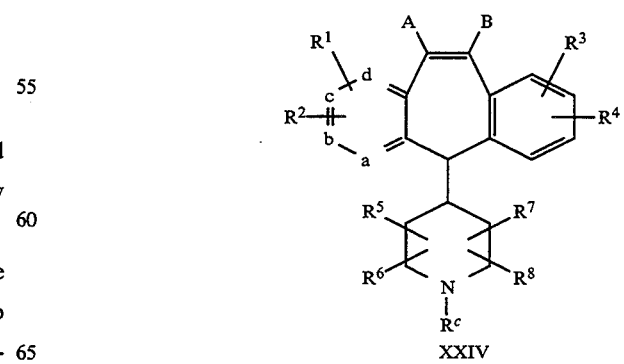

XXIV

Alternatively, the double bond can be isomerized to the bridgehead using a superacid, such as triflic acid at high temperature (e.g. 150°-200° C.) to produce Compound XXV. Subsequent catalytic hydrogenation preferably using Rh or Ru will then provide Compound XXIV.

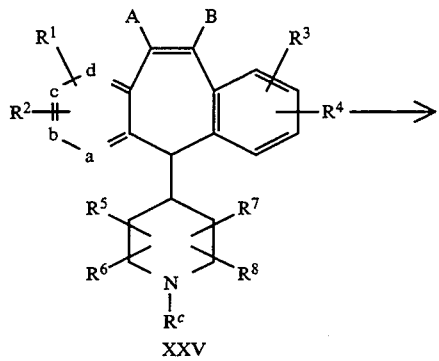

XXV

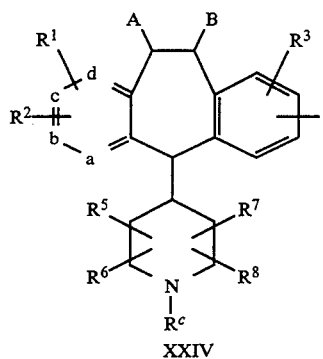

XXIV

When $R^c$ is C(Z)R the compounds of formula XXIV are compounds of the present invention. When $R^c$ is H, alkyl or $CO_2R^a$ the compounds are converted to compounds of the present invention as previously described.

C. A third method for the preparation of the subject compounds is by the use of the appropriately substituted Grignard reagent XXVI (or other corresponding metalated reagent M, e.g., organolithium, etc.). Compound XXVI can be reacted with compound XVII where L is a leaving group (e.g. chloride) to provide the desired Compound XXI.

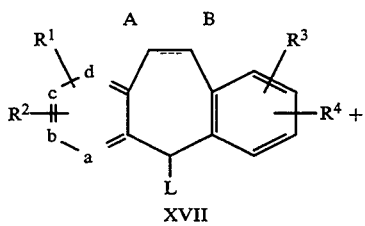

XVII

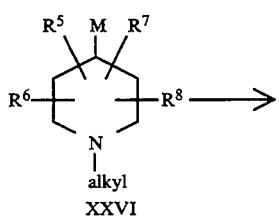

XXVI

-continued

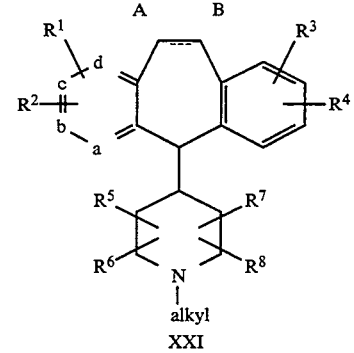

XXI

These reactions generally are conducted in an inert solvent such as ether, toluene, or THF at a temperature range of about −78° to about +50° C.

Alternatively, the metalating substituent and the leaving substituent could be interchanged and reacted under the same conditions to produce the same compound XXI.

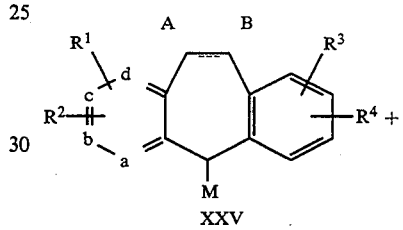

XXV

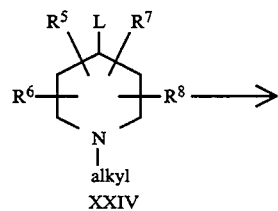

XXIV

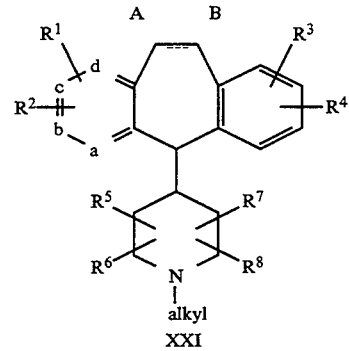

XXI

Compound XXI can be converted to compounds of the invention as previously described. Further details on these processes are described in U.S. Pat. Nos. 3,419,565; 3,326,924; 3,357,986 and in Org. Chem. 50 p. 339 (1985).

D. Alternatively, compounds of formulae XXVI and XXVII, the preparation of which is disclosed in U.S. Pat. Nos. 3,419,565; 3,326,924; and 3,357,986, can be used to provide Compound XXI. This can be accomplished by reductive removal of the alcohol under a variety of conditions e.g. the methods disclosed in J.A.C.S. 104 p. 4976 (1982) and in J. Org. Chem. 50 p. 339 (1985).

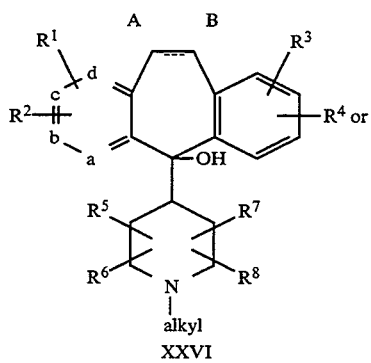

XXVI

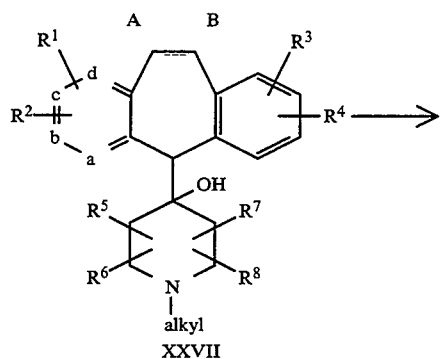

XXVII

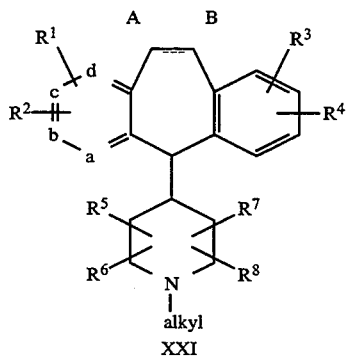

XXI

Compound XXI may be converted to compounds of the present invention as previously described.

SUBSTITUTION ON THE BRIDGEHEAD

The following process may be employed to produce compounds of structural formula I substituted at one or more of the bridgehead carbon atoms. For the compounds XXX through XXXIII which are substituted at one bridgehead carbon atom, the substitution group shown may have a bond drawn into the cycloheptane ring through the bridgehead, rather than to a specific bridgehead carbon atom. This is used to indicate that attachment of the substitution group to a particular bridgehead carbon atom is a function of the starting compound. For example, if the methoxy group of compound XXXI below is attached to bridgehead carbon 5, the carbonyl group on the bridgehead of compound XXXIII will be positioned at carbon 5 also. However, both isomers substituted at positions 5 and/or 6 are contemplated as being within the scope of the invention.

By substituting an isomer of the precursor compound, a compound can be synthesized having the substitution on the bridgehead carbon atoms different from that disclosed in the drawing.

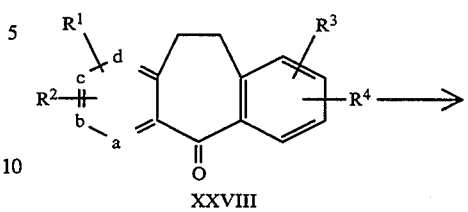

XXVIII

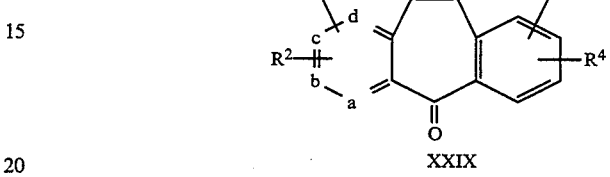

XXIX

The bridgehead of Compound XXVIII, which is disclosed in U.S. Pat. No. 3,326,924, is first brominated with an appropriate brominating agent, such as N-bromosuccinimide (NBS) in the presence of an initiator, such as azobisisobutyryl nitrile (ABIN), benzoyl peroxide or the like in an inert solvent, such as CCl4, benzene or a similar solvent. Heat or light may be required to initiate the reaction. The bromine on the bridgehead may then be eliminated with base to form the olefinic Compound XXIX. Examples of suitable bases for elimination include diazabicycloundecane (DBU), diazabicyclononane (DBN) and diazabicyclooctane (DABCO). Elimination is typically performed in an inert solvent at reflux temperature. Examples of suitable inert solvents include CH2Cl2, CCl4, toluene, tetrahydrofuran (THF), dioxane, and CHCl3, with CHCl3 being preferred.

Alternatively, Compound XXVIII may be refluxed in the presence of an oxidizing agent to yield compound XXIX. Representative examples of oxidizing agents suitable for oxidizing Compound XXVIII include 2,3-dichloro-5,6-dicyano-1,4-quinone (DDQ) and SeO2.

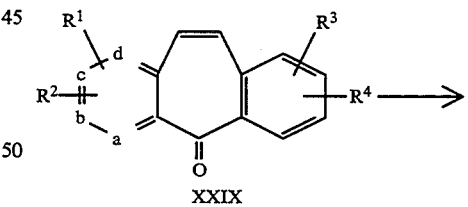

XXIX

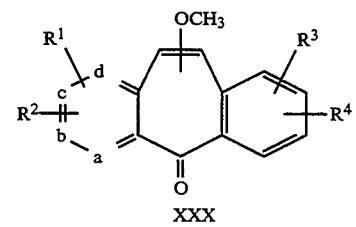

XXX

Compound XXIX may be converted to Compound XXX by adding excess powdered AgNO3 in methanol, followed by the addition of excess Br2, which bromoetherificates the unsubstituted bridgehead carbon atom. The bridgehead bromine is then eliminated with excess base, such as DBU to provide a compound of formula XXX. The reaction may be run in an inert solvent such as CHCl₃ at reflux temperature. The resultant isomeric mixture may be separated by column chromatography or any other appropriate method.

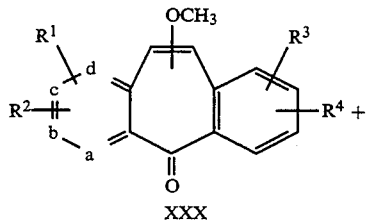
XXX

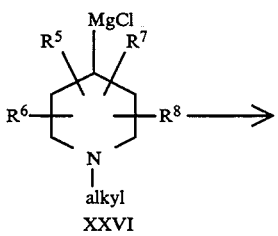
XXVI

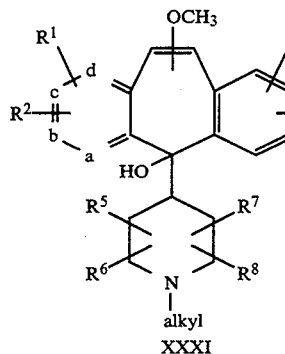
XXXI

A compound of formula XXXI is prepared by treating the 5-substituted or 6-substituted isomer represented by compound XXX with a Grignard reagent XXVI or similar metalated reagent in an inert solvent, such as ether, benzene, or tetrahydrofuran (THF). Compound XXVI is prepared in a known manner from magnesium and the 4-chloro N-substituted piperidine. The reaction may be refluxed if necessary, after which it may be quenched with NH₄Cl to form compound XXXI.

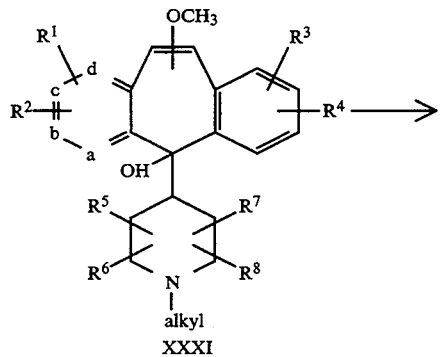
XXXI

-continued

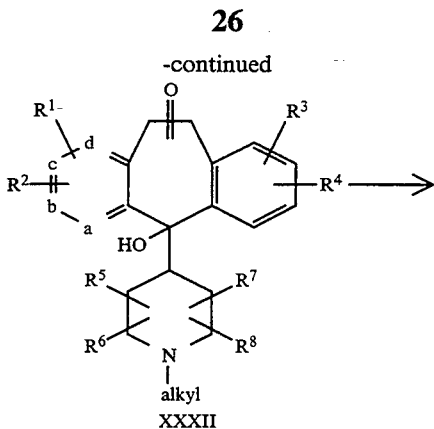
XXXII

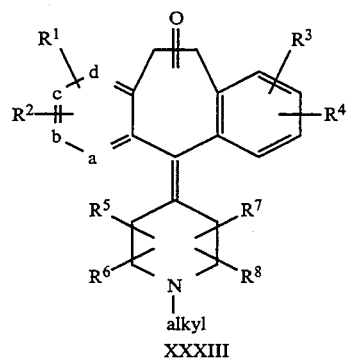
XXXIII

A compound of formula XXXI may be hydrolyzed with any strong, aqueous acid, for example, 80–95% H₂SO₄ or HCl, having a pH less than 1, at a temperature not higher than room temperature for not generally longer than one hour to produce an intermediate compound of formula XXXII.

After complete hydrolysis, compound XXXII may be dehydrated with CF₃SO₃H (triflic acid) or a similar acid to yield compound XXXIII. Examples of other acids for dehydrating compound XXXII at carbon atom 11 include, for example, HF/BF₃, CH₃SO₃H/BF₃, etc. The reaction can be performed in the absence of or with an inert co-solvent such as CH₂Cl₂. The temperature and time of the reaction vary with the acid employed. When triflic acid is used as the super acid system, the temperature may be controlled to minimize side reactions. For example, Compound XXXII having a carbonyl at carbon atom 5 is best dehydrated when the temperature is maintained in the range of from about 40° C. to about 80° C., preferably about 75° C. Alternatively, dehydration of a compound having a carbonyl at carbon atom 6 is best accomplished at elevated temperatures, such as from about 100° C. to 130° C.

Compound XXXIII can then be converted to compounds of the invention as previously described.

Ketone XXX can be reduced to the corresponding alcohol XXXIV using a variety of reducing agents (e.g. NaBH₄ in MeOH, LiAlH₄ in ether). The alcohol can then be converted to an appropriate leaving group (L) such as halide (e.g. Cl, Br, I) or other derivative (e.g. tosyloxy) thereby providing compound XXXV. For example, the chloride of XXXV (L=Cl) can be obtained from the alcohol using SOCl₂ in an inert solvent such as toluene.

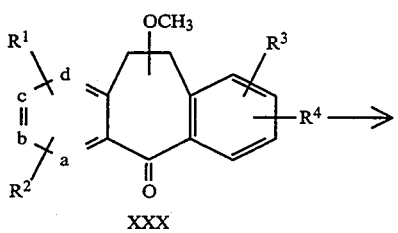

XXX

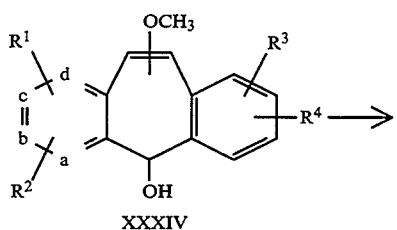

XXXIV

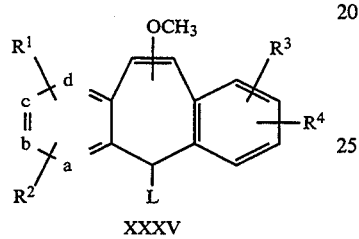

XXXV

Alkylation of the appropriately substituted piperazine compound XVI with XXXV then provides XXXVI. The reaction is usually conducted in an inert solvent such as THF or toluene, optionally with base, such as triethylamine or potassium carbonate, typically at ambient to reflux temperature.

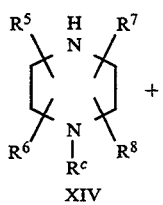

XIV

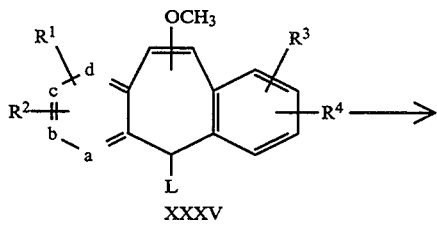

XXXV

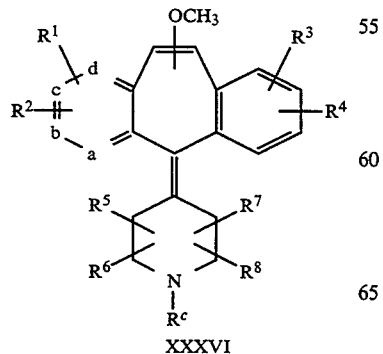

XXXVI

Compound XXXVI can then be hydrolyzed with any strong aqueous acid, for example 80–95% $H_2SO_4$ or HCl to provide the desired keto compound XXXVII.

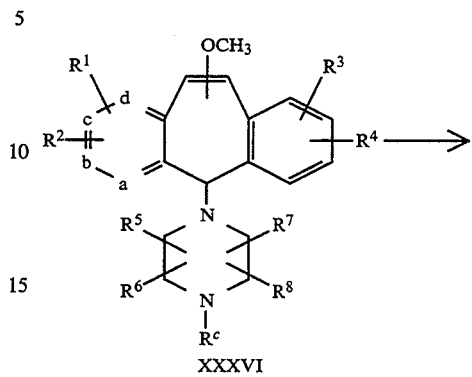

XXXVI

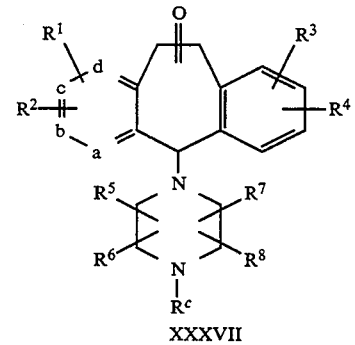

XXXVII

The bridgehead carbonyl of compound XXXVIII or XXXIII may be reduced to an hydroxy group by treating compound XXXVIII with an appropriate reducing agent, such as $NaBH_4$ in $CH_3OH$ or $LiAlH_4$ in ether to produce a compound of formula XXXIX.

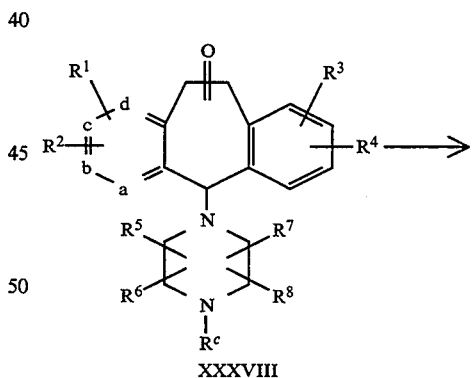

XXXVIII

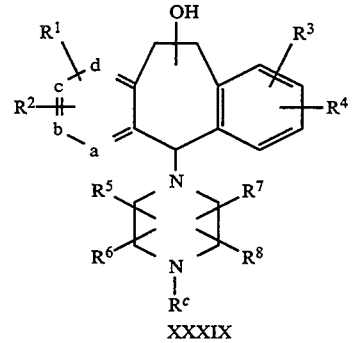

XXXIX

Compounds XXXIX, XXXVII or XXXII may be used to generate other substitutions in the bridgehead using available methods.

When $R^c$ is C(Z)R, compounds of the invention are prepared. When $R^c$ is H, $CO_2R^a$ or alkyl, such compounds can be converted to compounds of the invention as previously described.

Where Z represents sulfur, a compound of formula I where Z is oxygen is reacted with $P_2S_5$, Lawesson's reagent, or another reagent capable of introducing sulfur in place of oxygen.

The reaction may take place at elevated temperature in pyridine, toluene or other suitable solvents. Lawesson's reagent has the formula

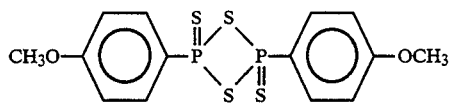

In this and other reactions, numerous conversions of a compound of formula I (Z=O) to another compound of formula I (Z=S) are possible.

In the above processes, it is sometimes desirable and/or necessary to protect certain $R^1$, $R^2$, $R^3$ and $R^4$ etc., groups during the reactions. Conventional protecting groups are operable. For example, the groups listed in column 1 of the following table may be protected as indicated in column 2 of the table:

| 1. Group to be Protected | 2. Protected Group |
| --- | --- |
| —COOH | —COOalkyl, —COObenzyl, —COOphenyl |
| \NH/ | N—$CO_2$alkyl, N—$CO_2$benzyl, N—$CO_2CH_2OCl_3$ |
| \C=O/ | (cyclic acetal groups) |
| —OH | —O—(tetrahydropyranyl), OCH_3 |
| —$NH_2$ | —N(phthalimido) |

Other protecting groups well known in the art also may be used. After the reaction or reactions, the protecting groups may be removed by standard procedures.

The compounds of the invention possess platelet-activating factor ("PAF") antagonistic properties. The compounds of the invention are, therefore, useful when PAF is a factor in the disease or disorder. This includes allergic diseases such as asthma, adult respiratory distress syndrome, urticaria and inflammatory diseases such as rheumatoid arthritis and osteoarthritis. For example, PAF is an important mediator of such processes as platelet aggregation, smooth muscle contraction (especially in lung tissue), vascular permeability and neutrophil activation. Recent evidence implicates PAF as an underlying factor involved in airway hyper-reactivity.

The PAF antagonistic properties of these compounds may be demonstrated by use of standard pharmacological testing procedures as described below. These test procedures are standard tests used to determine PAF antagonistic activity and to evaluate the usefulness of said compounds for counteracting the biological effects of PAF. The in vitro assay is a simple screening test, while the in vivo test mimics clinical use of PAF antagonists to provide data which simulates clinical use of the compounds described herein.

A. PAF ANTAGONISM ASSAY

In vitro Assay:

Preparation of platelet-rich plasma (PRP): Human blood (50 ml) was collected from healthy male donors in an anticoagulant solution (5 ml) containing sodium citrate (3.8%) and dextrose (2%). Blood was centrifuged at 110×g for 15 min. and the supernatant PRP carefully transferred into a polypropylene tube. Platelet-poor-plasma (PPP) was prepared by centrifuging PRP at 12,000×g for 2 min. in a Beckman Microfuge B. PRP was used within 3 hours of drawing the blood.

Platelet Aggregation Assay: When an aggregating agent such as PAF is added to PRP, platelets aggregate. An aggregometer quantifies this aggregation by measuring light (infra-red) transmission through PRP and comparing to PPP. The aggregation assays were performed using a dual-channel aggregometer (Model 440, Chrono-Log Corp., Hayertown, Pa.). PRP (0.45 ml) in aggregometer curettes was continually stirred (37° C.). Solutions of test compounds or vehicle were added to the PRP, and after incubation for 2 min., 10-15 μl aliquots of PAF solution were added so as to achieve a final concentration of $1-5 \times 10^{-8}$M. Incubations were continued until the increase in light transmission reached a maximum (usually about 2 min). Values for inhibition were calculated by comparing maximal aggregation obtained in the absence and the presence of the compound. For each experiment, a standard PAF antagonist, such as alprazolam, was used as a positive internal control. The inhibitory concentration ($IC_{50}$) is the concentration of compound in micromoles at which 50% of the aggregation is inhibited, as measured by the light transmission through each sample of PRP as compared to PPP. The test results are shown below in Tables Ia, Ib and Ic.

PAF is also a known bronchoconstrictive agent in mammals. Hence, PAF antagonism can be evaluated by measuring inhibition by the compounds of the invention in PAF-induced bronchoconstriction in guinea pigs.

B. PAF-INDUCED BRONCHOSPASM IN GUINEA PIGS

In Vivo Assay

Non-sensitized guinea Digs were fasted overnight, and the following morning were anesthetized with 0.9 ml/kg i.p. of dialurethane (0.1 g/ml of diallybarbituric acid, 0.4 g/ml of ethylurea and 0.4 g/ml of urethane). The trachea was cannulated and the animals were ventilated by a Harvard rodent respirator at 55 strokes/min. with a stroke volume of 4 ml. A side arm to the tracheal cannula was connected to a Harvard pressure transducer to obtain a continuous measure of intratracheal pressure, which was recorded on a Harvard Polygraph. The jugular vein was cannulated for the administration of compounds. The animals were challenged i.v. with PAF (0.4 ug/kg in isotonic saline containing 0.25% BSA) and the peak increase in inflation pressure that occurred within 5 min. after challenge was recorded. Test compounds were administered either orally (2 hrs. prior to PAF as a suspension in 0.4% methylcellulose vehicle) or intravenously (10 min. prior to PAF as a solution in dimethylsulfoxide).

The compound 8-chloro-11-(1-acetyl-4-piperidylidene)-6,11-dihydro-5H-benzo[5,6]cyclohepta[1,2-b]pyridine at a dose of 1 mg/kg given intravenously inhibited PAF-induced bronchospasm by 75% as measured by this procedure. Similarly, the compound 8-fluoro-11-(1-acetyl-4-piperidylidene)-6,11-dihydro-5H-benzo[5,6]cyclohepta[1,2-b]pyridine when administered at 3 mg/kg (iv) inhibited PAF-induced bronchospasm by 99%. The compound 9-fluoro-11-(1-acetyl-4-piperidylidene)-6,11-dihydro-5H-benzo[5,6]cyclopheta[1,2-b]pyridine when administered at 3 mg/kg (iv) inhibited PAF-induced bronchospasm by 97%.

The compounds of the invention also possess antihistaminic properties which may be assessed by test procedure C below. Test procedure C, "Prevention of histaminic-induced lethality" demonstrates basic antihistaminic activity of representative compounds of structural formula I. Protection against histamine lethality is indicative of strong antihistaminic properties.

Test procedures D, E and F demonstrate the extent of CNS activity induced by the compounds of the invention. The presence of strong CNS activity indicates a high probability of sedation caused by the compounds, a typically undesirable side effect of antihistamines. Consequently, a low level of CNS activity is preferred in most circumstances.

C. ANTIHISTAMINE ACTIVITY ASSAY

Prevention of Histamine-Induced Lethality in Guinea Pigs. Some of compounds shown below in Table I also were evaluated for antihistamine activity by their ability to protect female albino guinea pigs (250–350 g) against death induced by the intravenous injection of histamine dihydrochloride at 1.1 mg/kg, which is approximately twice the $LD_{99}$. Doses of the antagonists were administered orally to separate groups of fasted animals 1 hour prior to the challenge with histamine and protection from death recorded for 30 minutes after histamine. $ED_{50}$ values were determined for each drug by probit analysis.

CNS ACTIVITY ASSAYS

D. Antagonism of Physostigmine Lethality. The physostigmine-induced lethality test is indicative of CNS activity and the test described is a modification of the technique reported by COLLIER et al., *Br. J. Pharmac.*, 32, 295–310 (1968). physostigmine salicylate (1.0 mg/kg s.c.) produces 100% lethality when administered to mice grouped 10 per plastic cage (11×26×13 cm). Test agents were administered orally 30 minutes prior to physostigmine. The number of survivors were counted 20 minutes after physostigmine administration.

E. Antagonism of Acetic Acid Writhing. The acetic acid writhing test is a second test useful for determining CNS activity, and is essentially that described by HENDERSHOT and FORSAITH, *J. Pharmac. Exp. Ther.*, 125, 237–240 (1959), except that acetic acid rather than phenylquinone was used to elicit writhing. Mice were injected with 0.6% aqueous acetic acid at 10 mg/kg i.p. 15 minutes after oral administration of the test drug. The number of writhes for each animal was counted during a 10 minute period starting 3 minutes after acetic acid treatment. A writhe was defined as a sequence of arching of the back, pelvic rotation and hind limb extension.

F. Antagonism of Electro-Convulsive Shock (ECS). The ECS test is a third test useful for determining CNS activity. For the ECS test, a modification of the method of TOMAN et al., *J. Neurophysiol.*, 9, 231–239 (1946), was used. One hour after oral administration of the test drug or vehicle, mice were administered a 13 mA, 60 cycle a.c. electroconvulsant shock (ECS) for 0.2 seconds via corneal electrodes. This shock intensity produces tonic convulsions, defined as extension of the hind limbs, in at least 95% of vehicle-treated mice.

Of the above test procedures for measuring CNS activity, the physostigmine-induced lethality test is believed to be a major index of non-sedating characteristics, since it reflects mainly central anticholinergic potency which is believed to contribute to sedative activity.

Representative results of these test procedures with compounds of the invention are presented below in Tables IA, IB and IC.

TABLE IA

| Compound | Antihistaminic Activity Guinea pig oral dose | | CNS Activity | | | PAF Antagonism (in vitro) | |
| --- | --- | --- | --- | --- | --- | --- | --- |
| | | | Physostigmine lethality | Acetic writhing | ECS test | | |
| | (mg/kg) Dose | % Survival | $ED_{50}$ (mg/kg) | $ED_{50}$ (mg/kg) | $ED_{50}$ (mg/kg) | Dose (micromoles) | % PAF Antagonism |

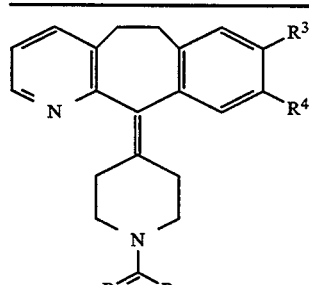

| | | | | | | | |
| --- | --- | --- | --- | --- | --- | --- | --- |
| Z = S, R = Ph | 5 PO | 60 | >320 | >320 | >320 | * | * |
| $R^3$ = Cl, $R^4$ = H | 1 PO | 0 | | | | | |
| Z = O R = $CH_3$ | 5 PO | 100 | >320 | >160 | >320 | 0.7 | 50 |

TABLE IA-continued

| | Antihistaminic Activity Guinea pig oral dose | | CNS Activity | | | PAF Antagonism (in vitro) | |
|---|---|---|---|---|---|---|---|
| | | | Physostigmine lethality | Acetic writhing | ECS test | | |
| Compound | (mg/kg) Dose | % Survival | $ED_{50}$ (mg/kg) | $ED_{50}$ (mg/kg) | $ED_{50}$ (mg/kg) | Dose (micromoles) | % PAF Antagonism |
| $R^3 = Cl\ R^4 = H$ | 1 PO | 60 | | | | | |
| $Z = O\ R = Ph$ | 5 PO | 100 | * | * | * | 10 | 9 |
| $R^3 = Cl\ R^4 = H$ | 1 PO | 0 | | | | | |
| $R = -CH_2OCH_3$ | 5 PO | 80 | >320 | >320 | >320 | 6 | 50 |
| $R^3 = Cl\ R^4 = H$ | 1 PO | 80 | | | | | |
| $Z = O$ | | | | | | | |
| $R = -CH_2CH_2CH_3$ | 5 PO | 100 | >320 | >320 | >320 | * | * |
| $R^3 = Cl\ R^4 = H$ | 1 PO | 40 | | | | | |
| $Z = O$ | | | | | | | |
| $R = -SCH_2CH_3$ | 5 PO | 80 | >320 | >320 | >320 | 10 | 0 |
| $R^3 = Cl\ R^4 = H$ | 1 PO | 100 | | | | | |
| $Z = O$ | | | | | | | |
| $R = CH_2CH_2$ | 5 PO | 80 | >320 | >320 | >320 | 3 | 60 |
| $R^3 = Cl\ R^4 = H$ | 1 PO | 40 | | | | | |
| $Z = O$ | | | | | | | |
| $R = -CH_2OCH_3$ | 5 PO | 100 | <320 | <320 | <320 | 10 | 9 |
| $R^3 = F\ R^4 = H$ | 1 PO | 100 | | | | | |
| $Z = O$ | | | | | | | |
| $R = -CH_3\ Z = O$ | 5 PO | 20 | * | * | * | 0.7 | 50 |
| $R^3 = F\ R^4 = H$ | | | | | | | |
| $R = -CH_3\ Z = O$ | 5 PO | $0^1$ | * | * | * | 0.9 | 50 |
| $R^3 = H\ R^4 = F$ | | | | | | | |
| $R^3 = Br, R^4 = H,$ | | | | | | 1.2 | 50 |
| $R = CH_3\ Z = O$ | | | | | | | |
| $R^3, R^4 =$  | | | | | | 5 | 35 |
| $R = CH_3$ | | | | | | | |
| $Z = O$ | | | | | | | |
| $R^3 = Cl, R^4 = H$ | | | | | | 25 | 63 |
| $R = CH=CH_2\ Z = O$ | | | | | | | |
| $R^3 = Cl, R^4 = H$ | | | | | | 50 | 29 |
| $R = NHCH_3$ | | | | | | | |
| $Z = O$ | | | | | | | |

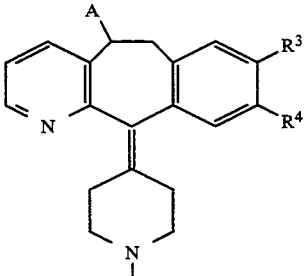

| | | | | | | | |
|---|---|---|---|---|---|---|---|
| $R^3 = Cl, R^4 = H$ | | | | | | 5 | 50 |
| $R = CH_3\ Z = O$ | | | | | | | |
| $A = OH$ | | | | | | | |
| $R^3 = Cl, R^4 = H$ | | | | | | 1.0 | 50 |
| $R = CH_3\ Z = O$ | | | | | | | |
| $A = CH_3$ | | | | | | | |
| $R^3 = Cl, R^4 = H$ | | | | | | 1.2 | 50 |
| $R = CH_3\ Z = O$ | | | | | | | |
| $A = Keto$ | | | | | | | |
| $R^3 = H, R^4 = H$ | $ED_{50} =$ 0.009 | | 6.1 | 8.9 | >80 | >100 | 50 |
| $A = H$ | | | | | | | |
| $CZR = CH_3**$ | | | | | | | |
| $R = OC_2H_5**$ | $ED_{50} =$ 0.19 | | >320 | >320 | >320 | 175 | 50 |
| $R^3 = Cl, R_4 = H$ | | | | | | | |
| $Z = O$ | | | | | | | |

*Not Tested
**Standard Known Antihistamine
[1]Expected to have some activity at a higher dose

TABLE IB

PAF Antagonism (in vitro)

| Compound | Dose (micromoles) | % PAF Antagonism |
|---|---|---|
| $R^3 = H, R^4 = H$<br>$R = CH_3\ Z = O$<br>$X = CH$ | 5 | 50 |
| $R^3 = Cl, X = N$<br>$R = CH_3\ Z = O$<br>$R^4 = H$ | .5 | 43 |
| $R^3 = Cl, X = N$<br>$R = H\ Z = O$<br>$R^4 = H$ | 5 | 50 |
| $R^3 = Cl, X = N$<br>$R = CH_2OCH_3$<br>$Z = O$<br>$R^4 = H$ | 5 | 50 |
| (structure with CH₃, Cl, piperidine with N-acetyl and CH₃) | 5 | 63 |

*Not tested
**Standard known antihistamine.

TABLE IC

PAF Antagonism (in vitro)

| Compound | Dose (micromoles) | % PAF Antagonism |
|---|---|---|
| (structure with Cl) | .5 | 50 |
| (structure with H₃C, Cl) | .12 | 44 |
| (N-oxide structure) | 1.5 | 50 |
| (structure with Cl, N-methyl, a₁⊖) | 5 | 58 |
| (structure with two F, N-oxide) | 2.5 | 53 |

As seen from the data of Tables IA, IB and IC and from the PAF induced bronchospasm inhibition test results, the compounds of structural formula I exhibit PAF antagonist and antihistaminic properties to varying degrees, i.e., certain compounds have strong PAF antagonistic activity, but have weaker antihistaminic activity. Other compounds are strong antihistamines but weaker PAF antagonists. Several of the compounds are both strong PAF antagonists and potent antihistamines. Consequently, it is within the scope of this invention to use each of these compounds when clinically appropriate. For example, if a strong PAF antagonist is required, but weaker antihistaminic activity is necessary, such a compound could be chosen by the clinician.

Alternatively, if both potent PAF antagonism and antihistaminic activity are required, a different compound of the invention would be utilized by the clinician.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 100 mg, according to the particular application. The appropriate dosage can be determined by comparing the activity of the compound with the activity of a known antihtstaminic compound such as 8-chloro-6,11-dihydro-11-(1-ethoxycarbonyl-4-piperidylidene)-5H-benzo[5,6]cyclohepta[1,2-b]pyridine, which compound is disclosed in U.S. Pat. No. 4,282,233.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be requlated according to the judgement of the attending clinician considering such factors as age, condition and size of the patient as well as severity of the symptom being treated. A typical recommended dosage regimen is oral administration of from 10 mg to 1500 mg/day preferably 10 to 750 mg/day, in two to four divided doses to achieve relief of the symptoms. The compounds are non-toxic when administered within this dosage range.

The following examples are intended to illustrate, but not to limit, the present invention.

PREPARATIVE EXAMPLE I

A.  N-(1,3-DIMETHYLETHYL)-3-METHYL-2-PYRIDINE CARBOXAMIDE

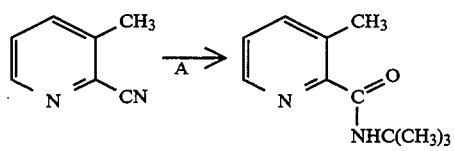

Suspend 2-cyano-3-methyl pyridine (400 g) in t-butanol (800 mL) and heat to 70° C. Add concentrated sulphuric acid (400 mL) dropwise over 45 minutes. Maintain the temperature at 75° C., until the reaction is complete, and for an additional 30 minutes. Dilute the mixture with water (400 mL), charge with toluene (600 mL) and bring to pH 10 with concentrated aqueous ammonia. Maintain the temperature at 50°–55° C. during the work up. Separate the toluene phase, and reextract the aqueous layer. Combine toluene phases and wash with water. Remove the toluene to yield the title compound N-(1,1-dimethylethyl-(3-methyl-2-pyridine carboxamide, as an oil, from which solid product is crystallized. (Yield 97%, as determined by an internal standard assay with gas chromatography).

B.  3-[2-(3-CHLOROPHENYL)ETHYL]-N-(1,1-DIMETHYLETHYL)-2-PYRIDINE CARBOXAMIDE

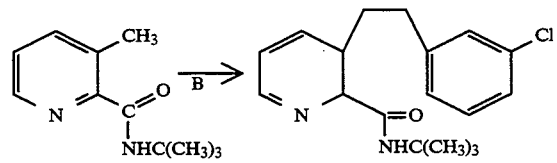

Dissolve the title compound of Preparative Example 1A, N-(1,1-dimethylethyl)-3-methyl-2-pyridine carboxamide (31.5 g.) in tetrahydrofuran (600 mL) and cool the resulting solution to −40° C. Add n-butyllithium (2 eg.) in hexane while maintaining the temperature at −40° C. The solution turns deep purple-red. Add sodium bromide (1.6 g) and stir the mixture. Add solution of m-chlorobenzylchloride (26.5 g., 0.174 mole) in tetrahydrofuran (125 mL) while maintaining the temperature at −40° C. Stir the reaction mixture until the reaction is complete as determined by thin layer chromatography. Add water to the reaction until the color is dissipated. Extract the reaction mixture with ethyl acetate, wash with water, and concentrate to a residue which is the title compound. (Yield 92% as shown by chromatography).

C. 3-[2-(3-CHLOROPHENYL)ETHYL]-2-PYRIDINE-CARBONITRILE

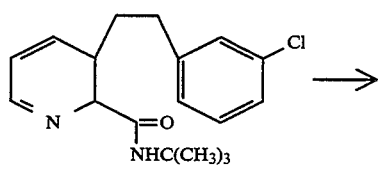

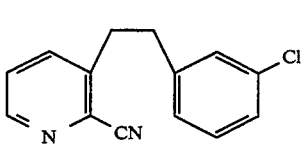

Heat a solution of the title compound of Preparative Example 1B, 3-[2-(3-chlorophenyl)ethyl]-N-(1,1-dimethylethyl)-2-pyridine carboxamide (175 g, 0.554 mole) in phosphorous oxychloride (525 mL, 863 g, 5.63 mole) and reflux for 3 hours. Determine completion of the reaction by thin layer chromatography. Remove any excess phosphorous oxychloride by distillation at reduced pressure and quench the reaction in a mixture of water and isopropanol. Bring to pH 5-7 by adding 50% aqueous sodium hydroxide solution while maintaining the temperature below 30° C. Filter the crystalline slurry of crude product and wash with water. Purify the crude product by slurrying the wet cake in hot isopropanol, and cool to 0°-5° C. Filter the product, wash with hexane and dry at a temperature below 50° C. to yield the title compound. (Yield: 118 g (HPLC purity 95.7%), m.p. 72° C.–73° C., 89.4% of theory).

D. 1-(METHYL-4-PIPERIDINYL)[3-(2-(3-CHLOROPHENYL)ETHYL)-2-PYRIDINYL]-METHANONE HYDROCHLORIDE

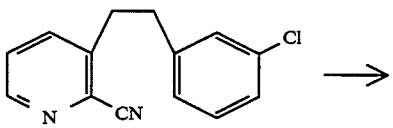

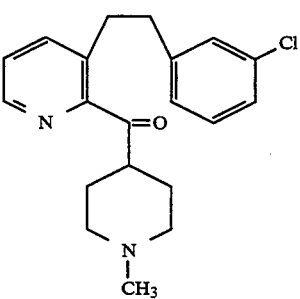

Dissolve the title compound of Preparative Example 1C, (118 g, 0.487 mole) in dry tetrahydrofuran (1.2L) and add N-methyl-piperidyl magnesium chloride (395 mL, 2.48 mole/liter, 0.585 mole, 1.2 eq.) over 15 minutes. Maintain the temperature at 40° C.–50° C. by cooling with water as necessary, for 30 minutes. Determine completion of the reaction by thin-layer chromatography. Quench the reaction by reducing the pH to below 2 with 2N HCl and stir the resulting solution at 25° C. for 1 hour. Remove the bulk of the tetrahydrofuran by distillation and adjust the resulting solution to pH 3.5 by addition of aqueous sodium hydroxide. Cool to 0° to 5° C. and filter off the crystalline hydrochloride salt product. Wash with ice cold water and dry to constant weight at 60° C. to yield the title compound. (Yield: 168.2 g (HPLC purity 94%), m.p. 183°–185° C. 89% of theory).

E. 8-CHLORO-11-(1-METHYL-4-PIPERIDYLIDENE)-6,11-DIHYDRO-5H-BENZO[5,6]CYCLOHEPTA[1,2-b]PYRIDINE

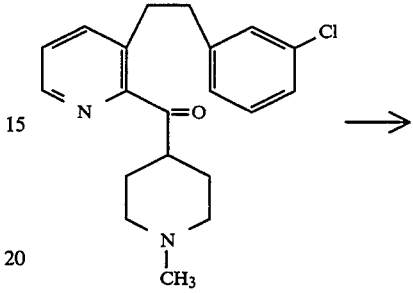

Dissolve the title compound of Preparative Example 1D above (59 g, 0.15 mole) in hydrofluoric acid (120 mL, 120 g, 6.0 mole) at −35° C. and add boron trifluoridine (44.3 g, 0.66 mole) over 1 hour. Determine completeness of the reaction by thin-layer chromatography. Quench the reaction using ice, water and potassium hydroxide bringing the solution to a final pH of 10. Extract the product with toluene and wash with water and brine. Concentrate the toluene solution to a residue, and dissolve in hot hexane. Remove the insolubles by filtration and concentrate the filtrate to yield the title compound as an off-white powder. (Yield: 45.7 g (HPLC purity: 95%), 92% of theory).

Alternative Step E: 8-CHLORO-11-(1-METHYL-4-PIPERIDYLIDENE)-6,11-DIHYDRO-5H-BENZO[5,6]CYCLOHEPTA[1,2-b]-PYRIDINE React the title compound of preparative Example 1D above (177 g, 0.49 mole) in trifluoromethanesulfonic acid (480 ml, 814.1 g, 5.31 mole) at 90°–95° C. for 18 hours under nitrogen. Determine the completeness of the reaction by thin-layer chromatography. Cool the reaction and quench the reaction with ice-water and adjust the pH to 6 with barium carbonate. Extract the product with methylene chloride, and concentrate under reduced pressure to about 1 liter. Wash with water, and extract the product into 1N HCl which is treated with 30 g of activated charcoal, and filter through celite. Adjust the pH of the filtrate to 10 with aqueous sodium hydroxide (50%), extract the product into methylene chloride, and remove under reduced pressure to form a residue. Dissolve the residue in hot hexane, and filter to remove insolubles. Concentrate the filtrate to yield the title compound as a beige powder. (Yield: 126 g (HPLC purity 80%), 65% of theory).

F. 8-CHLORO-11-(1-ETHOXYCARBONYL-4-PIPERIDYLIDENE)-6,11-DIHYDRO-5H-BENZO[5,6]CYCLOHEPTA[1,2-b]PYRIDINE

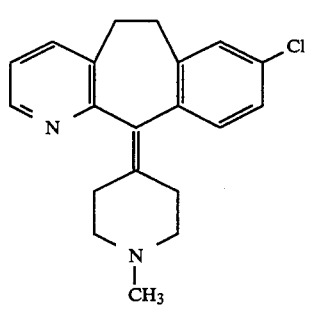

→

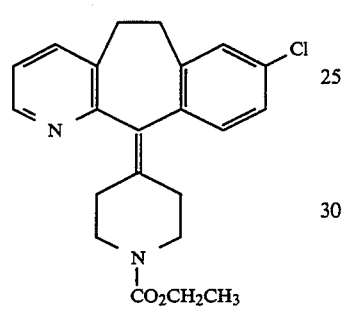

Dissolve the title compound of Preparative Example 1E above (45.6 g, 0.141 mole) in toluene (320 mL) at 80° C. and to it gradually add ethyl chloroformate (40.4 mL, 45.9 g, 0.423 mole). Following complete addition, maintain the temperature at 80° C. for 1 hour, then add diisopropylethylamine (2.7 mL, 2.00 g, 0.016 mole) and additional ethyl chloroformate (4.1 mL, 4.65 g, 0.0429 mole). Monitor completeness of the reaction by thin layer chromatography. Upon completion, cool the reaction mixture to ambient temperature, and wash the toluene solution with water. Concentrate the organic layer to a residue and dissolve in hot acetonitrile (320 mL). Decolorize the solution with 14 g of activated charcoal. Remove the activated charcoal by filtration and concentrate the filtrate to a crystalline slurry. Cool the mixture to 0°–5° C., and isolate the product by filtration. Wash with cold acetonitrile and dry the product at below 70° C. to yield the title compound. (Yield: 42.4 g (HPLC purity 97.4%), 80% of theory).

G. 8-CHLORO-11-(4-PIPERIDYLIDENE)-6,11-DIHYDRO-5H-BENZO[5,6]CYCLOHEPTA[1,2-b]PYRIDINE

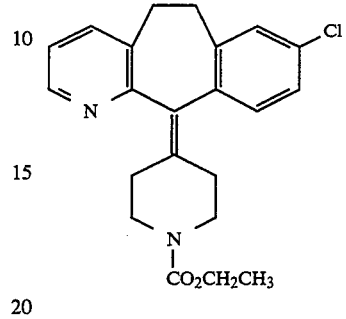

→

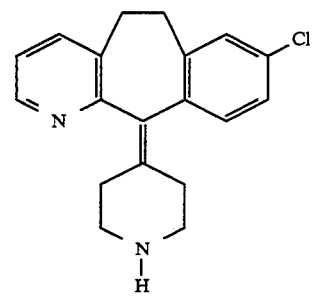

Hydrolize the title compound of Preparative Example 1E, 8-chloro-11-(1-methyl-4-piperidylidene)-6,11-dihydro-5H-benzo[5,6]cyclohepta[1,2-b]pyridine (39 g, 0.101 mole) with KOH (50 g) in ethanol (305 mL) and water (270 mL) at reflux under an argon atmosphere for 64 hours. Partially distill off the ethanol and dilute the residue with brine, and extract with ethylacetate (3×). Wash the co,Dined organic phases with water and dry with $Na_2SO_4$. Remove the solvent to give a solid which can be recrystallized from toluene to give the title compound as a white solid. (Yield: 24.5 g, 77%, melting point 154°–155° C.).

H. By substituting in step 1B above, an appropriately substituted aryl or alkyl halide listed in Table II below for meta-chlorobenzylchloride, and employing basically the same methods as steps C through G, the products listed in Table II are prepared by the process of Preparative Example 1 above. Reaction times are determined by TLC or HPLC. In some instances purification of the product by chromatography is necessary.

TABLE II

Product of step G

[Structure shown: tricyclic system with R³, R⁴ substituents on benzene ring, A substituent, and piperidylidene with N-C(=Z)-R group]

| | halide | R³ | R⁴ | A | Melting Point |
|---|---|---|---|---|---|
| 1. | BrCH₂-C₆H₄-F (3-F) | R³ = F, | R⁴ = H, | A = H | 133.5–134.5° C.[a] |
| 2. | ClCH₂-C₆H₃-(Cl)(Cl) (3,4-diCl) | R³ = Cl, | R⁴ = Cl, | A = H | 150–152° C.[b] |
| 3. | BrCH₂-C₆H₄-CH₃ (3-CH₃) | R³ = CH₃, | R⁴ = H, | A = H | 142–144° C.[c] |
| 4. | BrCH₂-C₆H₄-Br (3-Br) | R³ = Br, | R⁴ = H, | A = H | 146–148° C. |
| 5. | BrCH₂-C₆H₄-OCH₃ (3-OCH₃) | R³ = OCH₃, | R⁴ = H, | A = H | crude solid |
| 6. | BrCH₂-naphthyl | R³, R⁴ = (fused benzo ring) | | A = H | glass |
| 7. | CH₃I Then repeat step B with BrCH₂-C₆H₄-Cl (3-Cl) | R³ = Cl, | R⁴ = H, | A = CH₃ | glass |

[a] Step E required trifluoromethanesulfonic acid.
[b] Recrystallized from toluene.
[c] Recrystallized from acetone and pentane.

PREPARATIVE EXAMPLE 2

PREPARATION OF 9-FLUORO-11-(4-PIPERIDYLIDENE)-6,11-DIHYDRO-5H-BENZO[5,6]CYCLOHEPTA[1,2-b]PYRIDINE

A. N-(1,1-DIMETHYLETHYL)-3-[2-(4-FLUOROPHENYL)ETHYL]-2-PYRIDINE CARBOXAMIDE

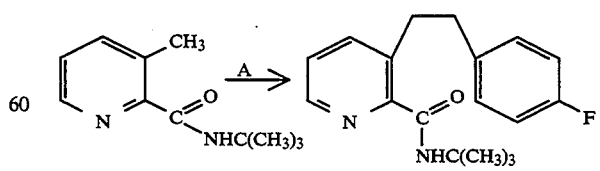

Cool a solution of N-(1,1-dimethylethyl)-3-methyl-2-pyridinecarboxamide (38.4 g, 0.2 mole) in dry THF (250 mL) to −40° C. and add n-butyl lithium (185 mL, 0.44 mole). Add sodium bromide (1.9 g, 18 mmol.) and stir for 15 minutes. Add 4-fluorobenzylchloride (31.8 g, 0.22 mole) and stir for 2.5 hours while warming to −5° C. Quench the reaction with water and extract the product twice with ethyl acetate, then wash with brine (2×). Dry the organic phase over Na₂SO₄, filter and remove the solvent to give the title compound. (60.0 g, Yield 99%, m.p. 59°-61° C.)

B. 3-[2-(4-FLUOROPHENYL)ETHYL]-2-PYRIDINE CARBONITRILE

Heat the title compound of Preparative Example 2A above (60.0 g,0.2 mole) in POCl₃ (200 mL) to 110° C. under an argon atmosphere for 3.5 hours. Pour the reaction mixture onto ice and basify with NaOH (50%) solution. Extract the mixture with ethyl acetate (3×) and wash with water. Wash with brine and dry over Na₂SO₄. Remove the solvent and pass the residue through a coarse SiO₂ (60–200 mesh) column to give the title compound as a white solid (40 g, Yield 88%, m.p. 48°-49° C.).

C. 9-FLUORO-5,6-DIHYDRO-(1H)-BENZO[5,6]CYCLOHEPTA[1,2-b]PYRIDIN-11-ONE

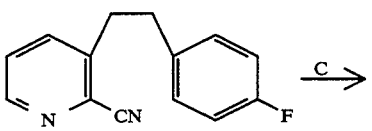

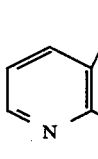

Cyclize the title compound of Preparative Example 2B above (31.5 g, 139 mmol) in polyphosphoric acid (1.24 kg) at 200° C. for 5.5 hours. Pour onto ice and basify with NaOH solution (50%). Extract the product with chloroform (3×) and wash with brine. Dry the organic phase with Na₂SO₄, filter and remove the solvent to give the title compound (20.4 g, yield 64%, m.p. 78°-81° C. after recrystallization from diisopropyl ether).

D. 9-FLUORO-11-(1-METHYL-4-PIPERIDINYL)-6,11-DIHYDRO-5H-BENZO[5,6]CYCLOHEPTA[1,2-b]PYRIDIN-11-OL

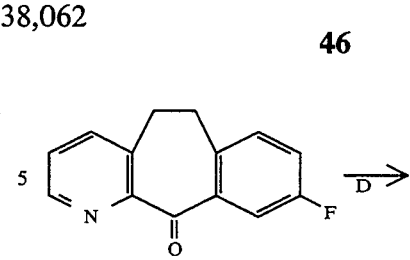

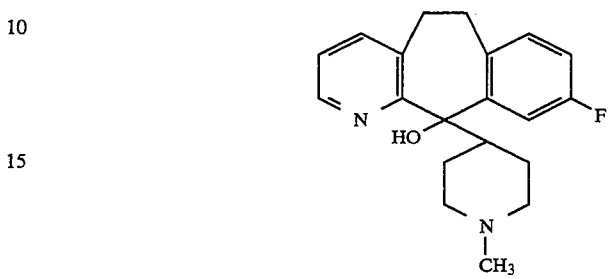

Dissolve the title compound of Preparative Example 2C above (10.0 g, 44 mmol) in THF (100 mL) and add slowly to a cooled (−40° C.) solution of the Grignard reagent prepared from N-methyl-4-chloro-piperidiene (57.9 ran, 88 mmol) in THF (70 mL). Stir the mixture for about 1 hour while warming up to 0° C. Quench the reaction with NH₄Cl solution and extract with ethyl acetate (2×). Wash the organic phase with brine and dry over Na₂SO₄, filter and remove the solvent. Purify the residue with flash chromatography and elute with methanol (5%) in CHCl₃ to give the title compound as white granular crystals. (10.1 g, Yield 70%, m.p. 126°-127° C. after recrystallization from diisopropyl ether.)

E. 9-FLUORO-11-(1-METHYL-4-PIPERIDYLENE)-6,11-DIHYDRO-5H-BENZO[5,6]CYCLOHEPTA[1,2-b]PYRIDINE

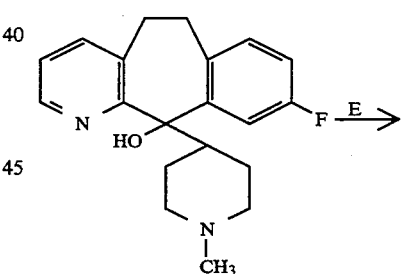

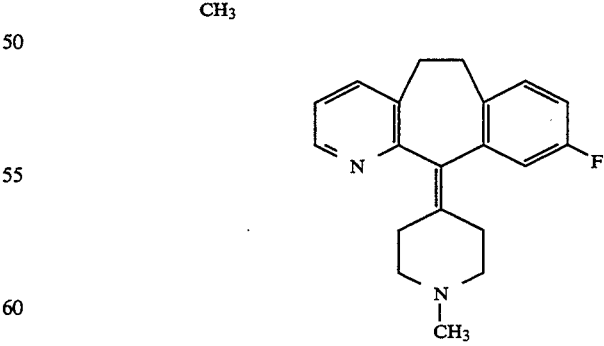

Add the title compound of preparative Example 2D above (7.3 g, 22.3 mmol) to a mixture of cooled H₂SO₄ and CF₃SO₃H (1:1), 146 mL). Stir the reaction mixture for 0.5 hours at ice bath temperature and then at room temperature for 1.5 hours. Pour the reaction mixture onto ice and basify with NaOH (50%) solution. Extract the product with ethyl acetate (3×) and wash with brine. Dry the organic phase over Na₂SO₄, filter and remove the solvent to give a crude oil. Charcoal the oil and recrystallize from ethyl acetate and isopropyl ether to give the title compound. (5.6 g, Yield 82%, m.p. 134.5°–135.5° C.).

F. 9-FLUORO-11-(1-ETHOXYCARBONYL-4-PIPERIDYLIDENE)-6,11-DIHYDRO-5H-BENZO[5,6]CYCLOHEPTA[1,2-b]PYRIDINE

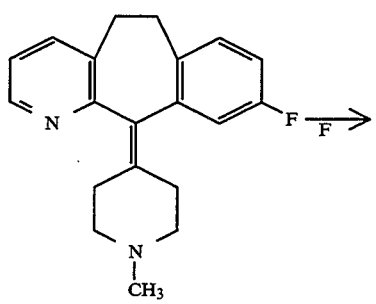

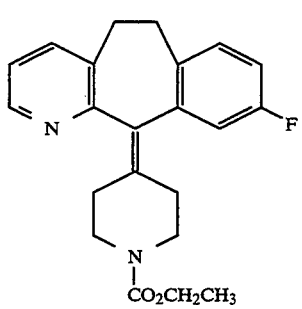

Stir a solution of the title compound of Preparative Example 2E above (5.0 g, 16.2 mmol) and triethylamine (2.6 g, 26 mmol) in dry toluene (60 mL) at 80° C. under an argon atmosphere, and add ethylchloroformate (9.8 g, 90 mmol) via a syringe. Stir the reaction at this temperature for 30 minutes and at room temperature for one hour. Filter the reaction and remove the solvent. Pass the residue through a coarse SiO₂ column (60–200 mesh), and elute with CHCl₃ to yield the title compound as a white solid. (4.5 g, Yield 76%, m.p. 112°–114° C. after trituration with pentane).

G. 9-FLUORO-11-(4-PIPERIDYLIDENE)-6,11-DIHYDRO-5H-BENZO[5,6]CYCLOHEPTA[1,2-b]PYRIDINE

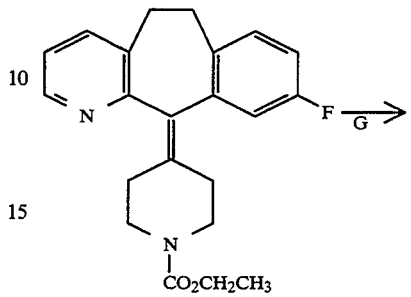

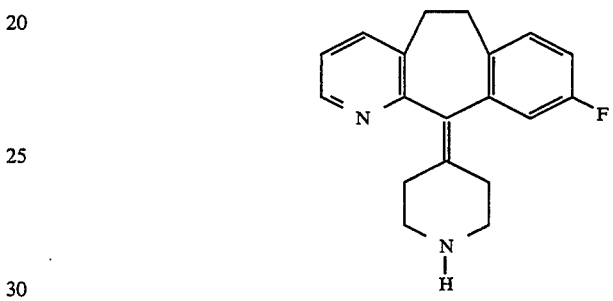

Reflux the title compound of Preparative Example 2F above (3.83 g, 10.4 mmol) with KOH (4.6 g) in 50 mL of ethanol/H₂O (1:1) for 4 hours under an argon atmosphere. Pour the reaction mixture into a brine solution and extract with ethyl acetate (2×), dry over Na₂SO₄ and filter. Remove the solvent to give the title compound (2.86 g, Yield 90%, m.p. 138°–140° C.).

H. By employing the appropriately substituted benzyl halide listed in Table III in place of 4-fluorobenzyl chloride in step 2A above, the desired products shown in the second column of Table III are prepared by employing basically the same process as described in steps 2A–2G. Workup time is determined by either TLC or HPLC. In some instances purification of the product by chromatography is necessary.

TABLE III

Product of Step G

| Benzyl Halide | | Melting Point |
|---|---|---|
| ClCH₂-C₆H₄-Cl | R³ = H, R⁴ = Cl | 134–135° C.ᵃ |

TABLE III-continued

Product of Step G

| Benzyl Halide | | Melting Point |
|---|---|---|
| ClCH₂—⟨benzene⟩—F | $R^3 = H, R^4 = F$ | 138–140° C.[b] |
| BrCH₂—⟨benzene⟩(F,F) | $R^3 = F, R^4 = F$ | 120–122° C.[b] |
| BrCH₂—⟨benzene⟩ | $R^3 = H, R^4 = H$ | 123–124° C. |

[a]Recrystallized from ethyl acetate and pentane.
[b]Triturated with pentane.

PREPARATIVE EXAMPLE 3

A. 6,11-Dihydro-11-(1-methyl-4-piperidylidene)-5H-benzo[5,6]cyclohepta[1,2-c]pyridine The compound 5,6-dihydro-11H-benzo[5,6]cyclohepta[1,2-c]pyridine-11-one, may be prepared by following the methods described in U.S. Pat. No. 3,419,565. This ketone may be converted to the title compound by the methods previously described in Preparative Example 2, steps D and E.

B. 11-(1-Cyano-4-piperidylidene)-6,11-DIHYDRO-5H-benzo[5,6]cyclohepta[1,2-c]pyridine

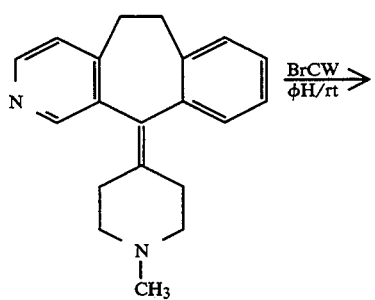

BrCW / φH/rt →

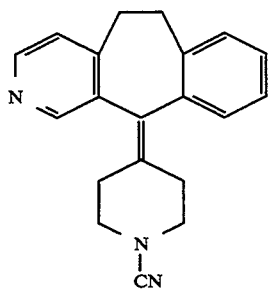

To a solution of 400 mg (1.35 mmole) of 11-(1-methyl-4-piperidylidene)-6,11-dihydro-5H-benzo[5,6]cyclohepta[1,2-c]pyridine in 5.0 mL of benzene at room temperature and under an argon atmosphere was added dropwise a solution of 168 mg (1.59 mmole) of cyanogen bromide in 4 mL of benzene. After 30 min. the mixture was poured into water and extracted once with EtOAc. The organic layer was isolated, washed once with brine, dried over Na₂SO₄, filtered, and concentrated in vacuo. The residue was purified via flash chromatography [2½% MeOH in CH₂Cl₂] to give 150 mg (37%) of the title compound as a solid: m.p. 212°–214° C.

C. 11-(4-piperidylidene)-6,11-dihydro-5H-benzo[5,6]cyclohepta[1,2-c]pyridine

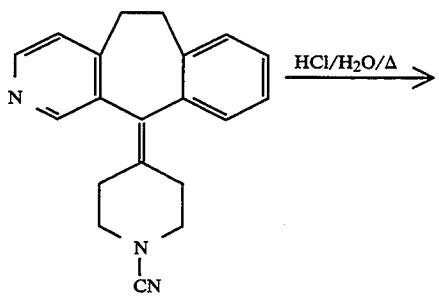

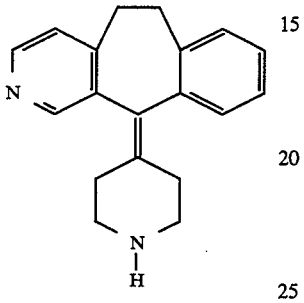

A mixture of 140 mg (0.46 mmole) of 11-(1-cyano-4-piperidylidene)-6,11-dihydro-5H-benzo[5,6]cyclohepta[1,2c]pyridine in 20 mL of 30% aqueous HCl was refluxed for about 22½ hrs. The mixture was poured into ice water, basified with 25% aqueous NaOH, and extracted twice with CH₂Cl₂. The combined organic portions were dried over Na₂SO₄, filtered, and concentrated in vacuo. The product was purified via flash chromatography [5% MeOH saturated with NH₃ in CH₂Cl₂] to give 95 mg (75%) of the title compound as a glass.

PREPARATIVE EXAMPLE 4

A. 8-Chloro-11H-benzo[5,6]cyclohepta[1,2-b]pyridin-11-one

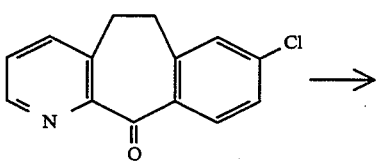

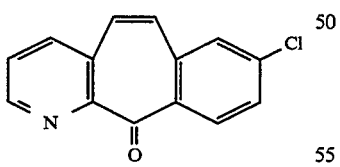

Reflux a mixture of 8-chloro-5,6-dihydro-1H-benzo[5,6]cyclohepta[1,2-b]pyridin-11-one (25.99 g, 0.107 mol.), recrystallized N-bromosuccinimide (21.35 g, 0.120 mol) and 167 mg (0.102 mmol) of azobisisobutyrylnitrile in 400 mL of carbontetrachloride under an argon atmosphere for 1.25 hours. Cool the solution slowly to 50° C. and filter off the resultant precipitate.

Reflux the precipitate with 1,8-diazabicyclo[5.4.0]undec-7-ene ("DBU") (20 mL, 0.134 mol) in CH₂Cl₂ (400 mL) for 1 hour. Wash with water (3×), dry over magnesium sulfate, filter and concentrate in vacuo. Recrystallize the crude product from CH₂Cl₂/toluene to give the title compound as colorless needles (8.93 g, yield 35%).

B. 8-Chloro-11-(1-methyl-4-piperidinyl)-11H-benzo[5,6]cyclohepta[1,2-b]pyridin-11-ol

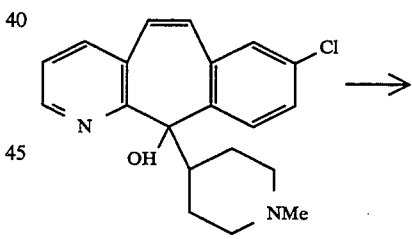

To a mixture of 22 mL of 0.5M Grignard reagent of N-methyl-4-chloropiperidiene (11.0 mmole) in THF at −45° C. and under a nitrogen atmosphere was added dropwise over 15 min. a solution of 1.06 gm (4.39 mmole) of 8-chloro-11H-benzo[5,6]cyclohepta[1,2-b]pyridin-11-one in 23 mL of dry THF. After 2 hr. 40 min. the reaction mixture was poured into water and extracted three times with EtOAc. The organic portions were combined, washed two times with brine, dried over MgSO₄, filtered, and concentrated in vacuo. The residue was purified via flash chromatography [10% MeOH in CH₂Cl₂] to give 970 mg (65%) of the title compound as a glass.

C. 8-Chloro-11-(1-methyl-4-piperidilidene)-11H-benzo[5,6]cyclohepta[1,2-b]pyridine

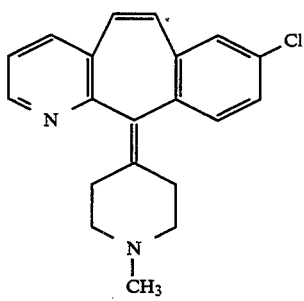

A mixture of 847 mg (2.48 mmole) of 8-chloro-11-(1-methyl-4-piperidinyl)-11H-benzo[5,6]cyclohepta[1,2-b]pyridin-11-ol in 5 mL of concentrated sulfuric acid and 5 mL of trifluoromethane sulfonic acid was heated at 70° C. for 4 hr 10 min. The mixture was cooled to room temperature, poured into ice cold 30% aqueous KOH, and extracted three times with CH₂Cl₂. The organic portions were combined, washed once with water, dried over MgSO₄, filtered, and concentrated in vacuo to yield 755 mg (94%) of the title compound as a glass.

D. 8-Chloro-11-[1-(2,2,2-trichloroethoxycarbonyl)-4-piperidylidene)-11H-benzo[5,6]cyclohepta[1,2-b]pyridine

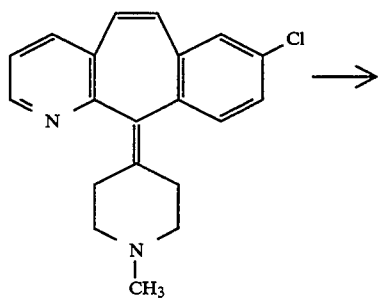

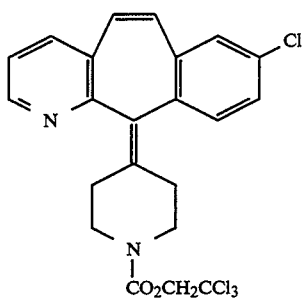

To a mixture of 755 mg (2.34 mmole) of 8-chloro-11-(1-methyl-4-piperidylidene)-11H-benzo[5,6]cyclohepta[1,2-b]pyridine and 1.5 mL of triethylamine in 25 mL of dry toluene at room temperature and under a nitrogen atmosphere was added 650 mL (4.72 mmole) of 2,2,2-trichloroethyl chloroformate. The mixture was then heated to 90° C. Additional amounts of the chloroformate (500 mL and 300 mL) and triethylamine (1.0 mL each time) were added to the mixture after 2 hr. and 3 hr. 40 min., respectively. After a total reaction time of 5 hr. the mixture was poured into water and extracted three times with CH₂Cl₂. The combined organic portions were dried over MgSO₄, filtered and concentrated in vacuo. The residue was purified via flash chromatography [1½% MeOH in CH₂Cl₂] to afford 639 mg (56%) of the title compound as a glass.

E. 8-Chloro-11-(4-piperidylidene)-11H-benzo[5,6]cyclohepta[1,2-b]pyridine

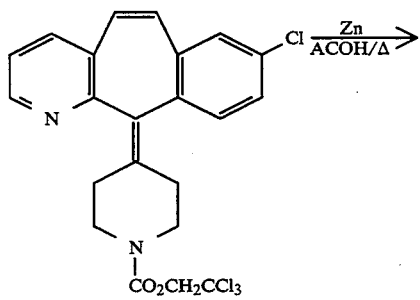

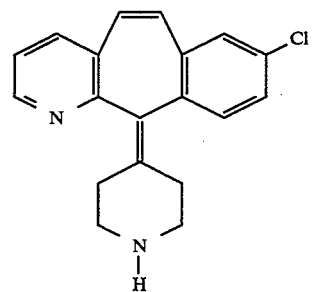

A mixture of 210 mg (0.434 mmole) of 8-chloro-11-[1-(2,2,2-trichloroethoxycarbonyl)-4-piperidylidene)-11H-benzo[5,6]cyclohepta[1,2-b]pyridine and 526 mg (8.05 mmole) of zinc dust in 4 mL of acetic acid was heated at 60°-70° C. After 2 hr. 20 min. another 547 mg (8.37 mmole) of zinc dust was added. After another 30 min. the mixture was basified with 10% aqueous NaOH and extracted four times with CH₂Cl₂. The combined organic portions were washed once with water, dried over MgSO₄, filtered, and concentrated in vacuo. The residue was purified via flash chromatography [5–6% MeOH/NH₃ in CHCl₃] to yield 71 mg (53%) of the title compound as a glass.

PREPARATIVE EXAMPLE 5

A. 5-Methoxy-8-chloro-11H-benzo[5,6]cyclohepta[1,2-b]pyridin-11-one
B. 6-Methoxy-8-chloro-11H-benzo[5,6]cyclohepta[1,2-b]pyridin-11-one

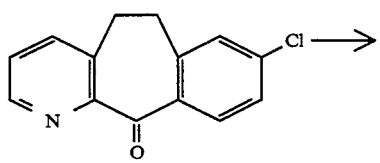

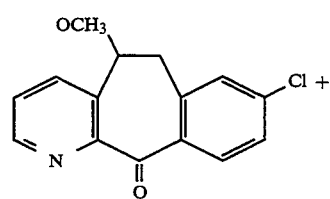

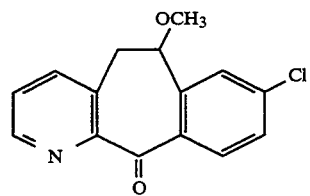

Add Br₂ (5.10 mL, 99 mmol) to a mixture of 8-chloro-11H-benzo[5,6]cyclohepta[1,2-b]pyridin-11-one (8.15 g, 33.7 mmol) and powdered AgNO₃ (23.19 g, 137 mmol) in 300 mL of dry methanol at room temperature under an argon atmosphere. After 8 hours, add additional AgNO₃ (5.90 g, 34.7 mmol) followed by additional Br₂ (1.7 mL, 33.0 mmol). After 0.5 hours pour the mixture into water and extract (4×) with CH₂Cl₂. Combine the organic phases, dry over magnesium sulfate, filter and concentrate in vacuo to give a mixture of the crude bromo ethers.

Dissolve the crude product in CH₂Cl₂ (200 mL) at room temperature and place under an argon atmosphere. Add DBU (20 mL, 134 mmol) and reflux for 1.3 hours. Add additional DBU (10 mL, 67 mmol) and reflux the mixture for an additional hour. Pour the mixture into water and extract (3×) with CH₂Cl₂. Combine the organic phases, wash with water and dry over magnesium sulfate. Filter and concentrate in vacuo. The two isomeric vinyl ethers, title compounds A and B, are separated via flash chromatography [40%–75% ethyl acetate in hexanes] and recrystallize from ethyl acetate hexanes to give title compound A (1.51 g, 14.3%, mp 156° to 158° C.) and title compound B (3.68 g, 35%, mp 161° to 162° C.).

C.  5-Methoxy-8-chloro-11-(1-methyl-4-Piperidinyl)-11H-benzo[5,6]cyclohepta[1,2-b]pyridin-11-ol

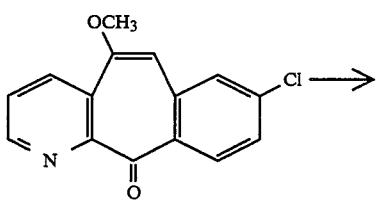

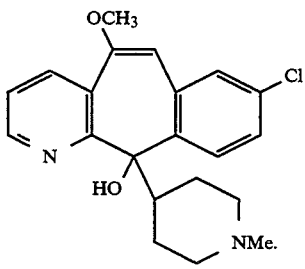

Add a 1.5M Grignard solution of N-methyl 4-chloropiperidine (150 mL, 22.5 mmol) in THF dropwise over a 7 minute period to 5-methoxy-8-chloro-11H-benzo[5,6]cyclohepta[1,2-b]pyridin-11-one (5.00 g, 18.4 mmol) in THF (70 mL) at 0° C. and under an argon atmosphere. Quench the reaction after 30 minutes with a saturated solution of NH₄Cl (pH 8) and extract (3×) with CHCl₃. Combine the organic portions, wash with brine, dry over sodium sulfate, filter and concentrate in vacuo. Purify via flash chromatography (CH₃OH 5% in CH₂Cl₂) to give the title compound (3.60 g, 53%) as a solid. The solid may be recrystallized from isopropyl ether to give a white powder (mp 168°–170° C.).

D.  8-Chloro-11-(1-methyl-4-piperidylidene)-6,11-dihydro-5H-benzo[5,6]cyclohepta[1,2-b]pyridin-5-one

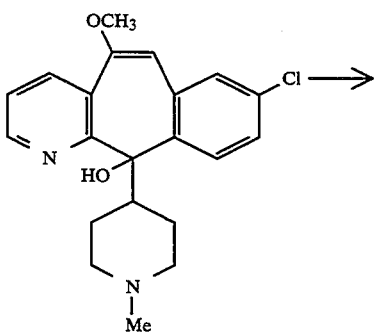

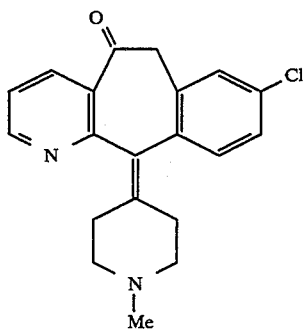

Dissolve 5-Methoxy-8-chloro-11-(1-methyl-4-piperidinyl)-11H-benzo[5,6]cyclohepta[1,2-b]pyridin-11-ol (4.26 g) in CH₃OH (6 mL) at 0° C. under an argon atmosphere. Add slowly a cooled solution of 92% aqueous H₂SO₄ (54 mL). Allow the mixture to warm to room temperature for 35 minutes. Pour the solution onto ice, basify with aqueous NaOH (25%), and extract with methylene chloride (3×). Combine the organic portions, wash with brine and dry over sodium sulfate. Filter and concentrate in vacuo. Triturate the residue with ispropyl ether to give an intermediate, 8-chloro-11-hydroxy-11-(1-methyl-4-piperidinyl)-6,11-dihydro-5H-benzo[5,6]cyclohepta[1,2-b]pyridin-5-one as a white solid (3.58 g., 92%, m.p. 170° to 174° C. as HCl salt).

Dissolve the intermediate compound (3.58 g, 10.0 mmol) in trifluoromethane sulfonic acid (50 mL) and heat to 45° C. under an argon atmosphere for 3 hours. Pour the mixture onto ice, basify with aqueous NaOH (25% w/v), and extract with CHCl₃ (3×). Combine the organic portions, wash with brine and dry over sodium sulfate. Filter and concentrate in vacuo. Chromatograph on silica gel (5% CH₃OH in CH₂Cl₂) to give the title compound as an off white solid (1.703 g, 50%, 58% based on recovered starting material). An analytical sample was prepared by recrystallization of the product with ethyl acetate/isopropyl ether (mp 162°–163° C.).

E.  Ethyl-4-(8-chloro-5-ethoxycarbonyloxy-11H-benzo[5,6]cyclohepta[1,2-b]pyridin-11-ylidene)-1-piperidine carboxylate

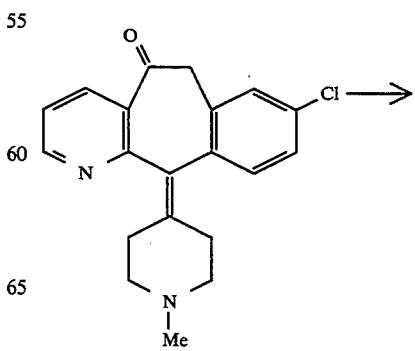

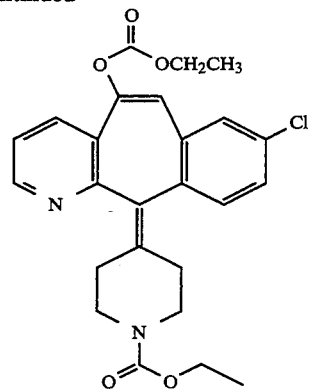

Dissolve the 8-Chloro-11-(1-methyl-4-piperidylidene)-6,11-dihydro-5H-benzo[5,6]cyclohepta[1,2-b]pyridin-5-one (617 mg, 1.82 mmol) and triethylamine (0.50 mL, 3.58 mmol) in toluene (12 mL) at 80° C. under an argon atmosphere. Add dropwise over 2 minutes ethyl chloroformate (0.87 mL, 9.10 mmol). After 25 minutes cool the mixture to room temperature, filter, and concentrate in vacuo. Purify the crude product via flash chromatography (1% CH₃OH in CH₂Cl₂) to yield the title compound as a glass (834 mg, 98%).

F. 8-Chloro-11-(4-piperidylidene)-6,11-dihydro-5H-benzo[5,6]cyclohepta[1,2-b]pyridin-5-one

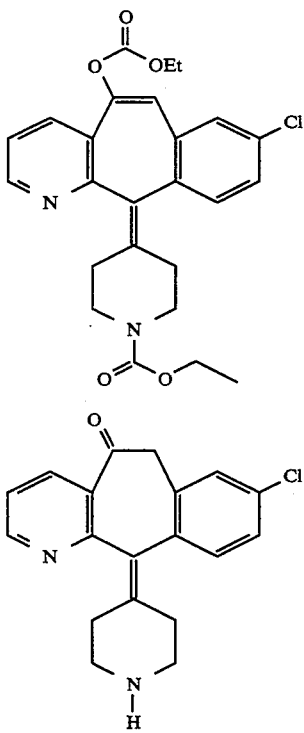

Mix ethyl 4-(8-chloro-5-ethoxycarbonyloxy-11H-benzo[5,6]cyclohepta[1,2-b]pyridin-11-ylidene)-1-piperidine carboxylate (897 mg, 1.91 mmol) and aqueous KOH (20 mL, w/v) in ethanol (15 mL) and reflux under an argon atmosphere for 25 hours. Pour the mixture into water and extract with CHCl₃ (3×). Combine the organic portions, wash with brine, dry over sodium sulfate, filter, and concentrate in vacuo. Purify the residue via flash chromatography (2% CH₃OH saturated with NH₃ in CH₂Cl₂) and triturate with isopropyl ether to give the title compound as a white solid (417 mg, 67%, mp 194°–196° C. (dec)).

G. 5-Hydroxy-8-chloro-11-(4-piperidylidene)-6,11-dihydro-5H-benzo[5,6]cyclohepta[1,2-b]pyridine

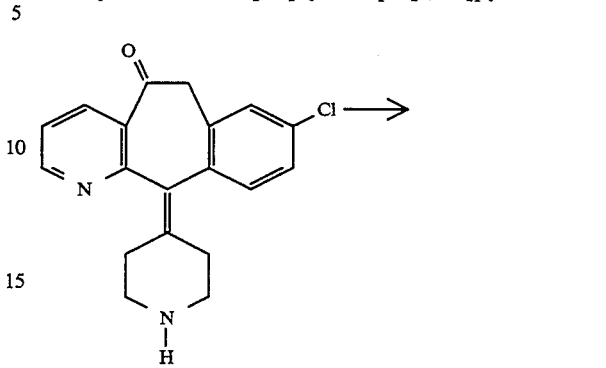

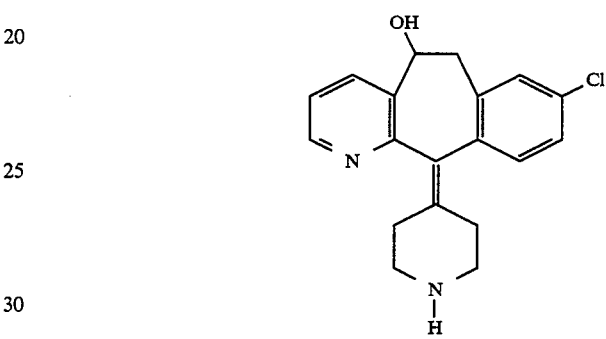

Mix 8-Chloro-11-(4-piperidylidene)-6,11-dihydro-5H-benzo[5,6]cyclohepta[1,2-b]pyridin-5-one (400 mg, 1.23 mmol) in CH₃OH (20 mL) at 0° C. under an argon atmosphere, and add in 3 portions NaBH₄ (total 231 mg, 6.10 mmol). After 30 minutes, pour the mixture into water and extract (3×) with ethyl acetate. Combine the organic portions, wash with brine, dry over sodium sulfate, filter and concentrate in vacuo. Triturate the solid with isopropyl ether/ethyl acetate to give the title compound as a white solid (351 mg, 87%).

PREPARATIVE EXAMPLE 6

8-CHLORO-11(Z)-2,5-DIMETHYL-4-PIPERIDYLIDENE)-6,11-DIHYDRO-5H-BENZO[5,6]CYCLOHEPTA[1,2-b]PYRIDINE

A. 1,2,6-trimethyl-4-chloropiperidine

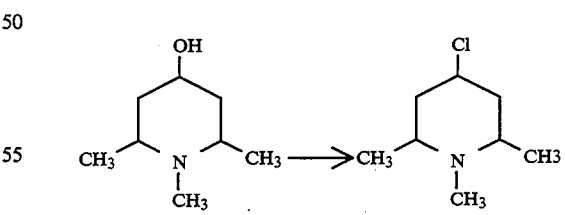

The starting material, 1,2,6-trimethyl-4-piperidinol, may be prepared by the method disclosed in Archi Kern, Volume 27, pages 189–192 (1955). To a cooled (icebath) solution of 1,2,6-trimethyl-4-piperidinol (12.2 g, 85.3 mmol) in 120 mL of dry benzene was slowly added thionylchloride (17 mL, 233 mmole). The dark reaction mixture was then warmed to 70° C. for 20 min. The reaction was cooled and then suspended in water followed by filtration. The filtrate was extracted once with diethylether. The aqueous layer was separated and then basified with 30% NaOH solution. The product was then extracted twice with CH₂Cl₂, washed once with brine, dried (Na₂SO₄), filtered and solvent removed to give a crude brown liquid which was distilled (2–4 mmHg, 62°–64° C.) to give the title compound (8.0 g, 58% yield).

B. 8-chloro-11-(1,2,6-trimethyl-4-piperidinyl)-6,11-dihydro-5H-benzo[5,6]cyclohepta[1,2-b]pyridin-11-ol

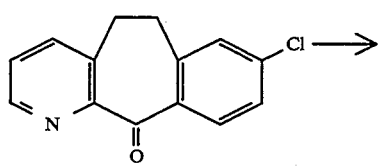

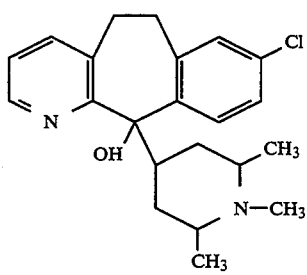

The chloride, 1,2,6-trimethyl-4-chloropiperidine, (4.2 g, 26 mmol) was slowly dripped into a solution of dry THF (18 mL) containing Mg (633 mg, 26.3 mm). The Grignard reagent was then formed after heating for 6 hours at 70° C.

To a cooled (ice-bath), stirred solution of 8-chloro-5,6-dihydro-11H-benzo[5,6]cyclohepta[1,2-b]pyridin-11-one (6.3 g, 26 mmol) in THF (50 mL) was added the above Grignard reagent. The reaction was allowed to stir for 1 hr. at this temperature and then quenched with NH₄Cl solution. The product was extracted 3× with EtOAc, washed once with brine, dried (Na₂SO₄), filtered and solvent removed to give a crude brown material which was chromatographed to give the title compound (5.1 g, 53% yield) as a yellowish glass.

C. 8-chloro-11-(1-methyl-(Z)-2,6-dimethyl-4-piperidylidene)-6,11-dihydro-5H-benzo[5,6]cyclohepta[1,2-b]pyridine

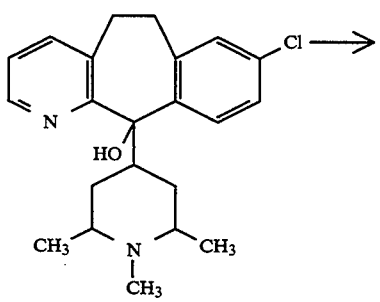

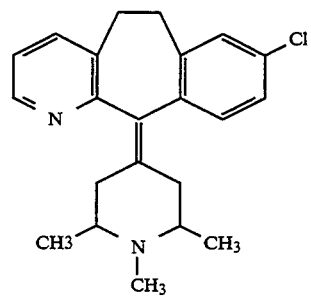

A mixture of 8-chloro-11-(1,2,6-trimethyl-4-piperidinyl)-6,11-dihydro-5H-benzo[5,6]-cyclohepta[1,2-b]pyridin-11-ol (5.0 g, 14.1 mmol) in 85% H₂SO₄(100 mL) was heated in an oil bath (60°–65° C.) for 3 hours. The reaction was cooled and diluted with water followed by basification with 25% aq. NaOH solution. The crude product was extracted with CH₂Cl₂, washed with brine, dried (Na₂SO₄), filtered and solvent removed. Purification and separation of the E and Z isomers via chromatography (2%→5% MeOH saturated with NH₃ in CH₂Cl₂) gave the title compound (300 mg, 6%).

D. 8-chloro-11-(1-cyano-(Z)-2,6-dimethyl-4-piperidylidene)-6,11-dihydro-5H-benzo[5,6]cyclohepta[1,2-b]pyridine

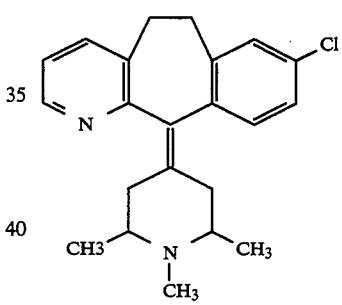

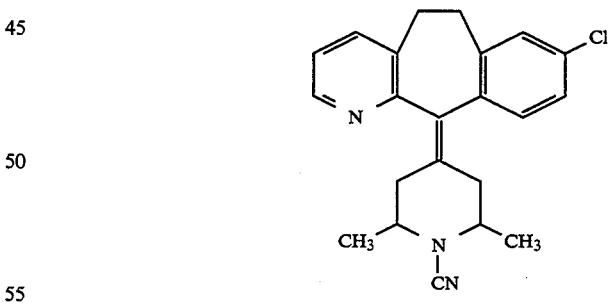

A solution of 300 mg (0.85 mmol) of 8-chloro-11-(1-methyl-(Z)-2,6-dimethyl-4-piperidylidene)-6,11-dihydro-5H-benzo[5,6]cyclohepta[1,2-b]pyridine in benzene (4.5 mL) was slowly dripped into a stirred solution of BrCN (133 mg, 1.2 mmol) in benzene (4.5 mL) at room temperature. This was allowed to stir for 2½ hr under argon. The reaction mixture was suspended between water and EtOAc. The EtOAc layer was washed with brine and dried (NaSO₄). After filtration the solvent was removed and the crude material was chromatographed (3% MeOH in CH₂Cl₂) to give the title compound (251 mg, 81% yield).

E. 8-chloro-11-((Z)-2,6-dimethyl-4-piperidylidene)-6,11-dihydro-5H-benzo[5,6]cyclohepta[1,2-b]pyridine

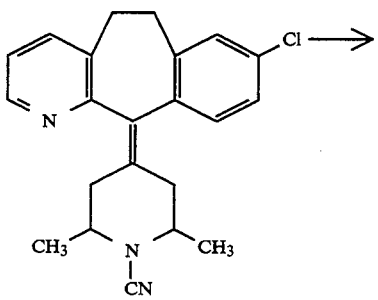

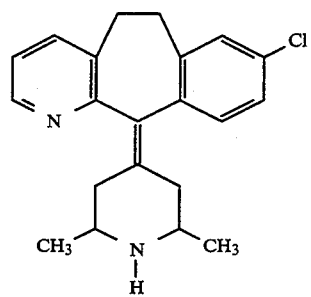

A mixture of 8-chloro-11-(1-cyano-(Z)-2,6-dimethyl-4-piperidylidene)-6,11-dihydro-5H-benzo[5,6 ]cyclohepta[1,2-b]pyridine (200 mg, 0.55 mmol) in 80% HCl (20 mL) was allowed to reflux for 7 hours. The mixture was cooled and then basified with 25% NaOH. The product was extracted 2× with CH₂Cl₂, separated, washed once with brine, dried (NaSO₄), filtered and solvent removed to give the title compound (174 mg, 93% yield) as a white glass.

F. By following similar procedures in steps D & E above, 8-chloro-11-(1-methyl-(E)-2,6-dimethyl-4-piperidylidene)-6,11-dihydro-5H-benzo[5,6]cyclohepta[1,2-b]pyridine was converted to 8-chloro-11-((E)-2,6-dimethyl-4-piperidylidene-6,11-dihydro-5H-benzo[5,6]cyclohepta[1,2-b]pyridine.

PREPARATIVE EXAMPLE 7

8-CHLORO-11-(4-PIPERIDYLIDENE)-6,11-DIHYDRO-3-METHYL-5H-BENZO[5,6]CYCLOHEPTA[1,2-b]PYRIDINE

A. 3,5-DIMETHYLPYRIDINIUM N-OXIDE

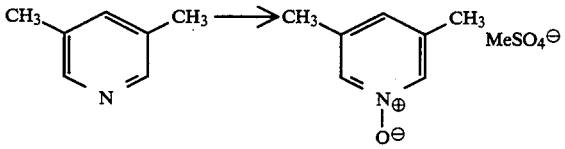

A solution of 285 mL (1.31 mol) of 35% peracetic acid was slowly added to a stirred solution of 149 g (1.39 mol) of 3,5-dimethylpyridine during which the temperature rose to 85° C. and was maintained at this temperature during addition. After the temperature of the mixture dropped to about 35° C. the reaction was stored at 5° C. overnight.

After partial removal of 185 ml of acetic acid via distillation under vacuum, the reaction was washed with NaHSO₄ solution and then neutralized with 10% NaOH solution to pH of about 7. The product was extracted with CH₂Cl₂ to give the title compound as a white solid (yield 142 g, 83%).

B. 1-METHOXY-3,5-DIMETHYLPYRIDINIUM METHYL SULFATE

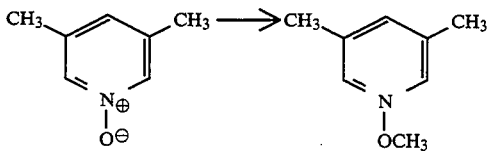

Dimethylsulfate (42.0 g, 0.33 mol) was slowly added to a mechanically stirred solids of 41.0 g (0.33 mol) of 3,5-dimethylpyridinium N-oxide. The mixture was then heated on a steam bath for 1 hr. Then vacuum was applied while cooling to give a brownish solid of the title compound in quantitative yield.

C. 2-CYANO-3,5-DIMETHYLPYRIDINE

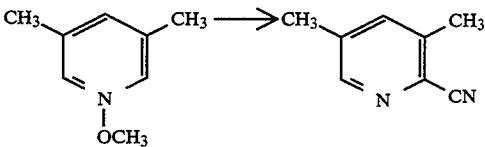

To a cooled (0° C.) solution of sodium cyanide (49.0 g, 0.999 mol, 3.0 eq.) in 135 mL of water (air free) was dripped 1-methoxy-3,5-dimethyl pyridinium methyl sulfate (83.0 g, 0.33 mol) in 100 mL water (air free) in 1¼ hr., keeping the temperature below 3° C. The reaction mixture was stored at about 3° C. overnight. The mixture was filtered and washed with water to give 40 g of the title compound. An analytical sample was recrystallized from isopropyl ether and pentane (4:1) (m.p. 61°–62° C.).

D. N-(11-dimethylethyl)-3,5-dimethyl-2-pyridine carboxamide

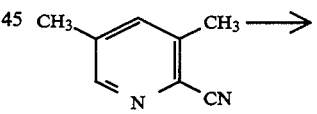

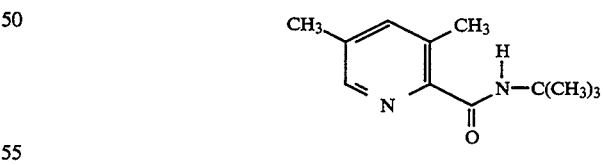

To a stirred solution of 20.3 g (0.153 mol) of 2-cyano-3,5-dimethylpyridine in 100 mL of acetic acid was added 20 mL of conc. sulfuric acid within 10 minutes (temp. rose to 35° C.), followed by 20 mL of t-butanol over an additional 15 minutes. The solution was warmed at 75° C. for 30 minutes after which it was cooled to room temperature and basified with 25% NaOH. The product was extracted 3× with EtOAc (600 mL), which was combined and washed 1× with brine, dried (Na₂SO₄), filtered and concentrated in vacuo to give the title compound (31.26 g) as a yellowish oil.

E. 8-Chloro-11-(4-piperidylidene)-6,11-dihydro-3-methyl-5H-benzo[5,6]cyclohepta[1,2-b]pyridine By substituting in step 1B above N-(1,1-dimethylethyl)-3,5-dimethyl-2-pyridine carboxamide for N-(1,1dimethylethyl)-3-methyl-2-pyridine carboxamide and employing basically the same methods as steps B through G, one obtains 8-chloro-11-(4-piperidylidene)-6,11-dihydro-3-methyl-5H-benzo[5,6]cyclohepta[1,2-b]pyridine. Reaction times are determined by TLC or HPLC.

PREPARATIVE EXAMPLE 8

11-(4-PIPERIDYL)-6,11-DIHYDRO-5H-BENZO[5,6-]CYCLOHEPTA[1,2-b]PYRIDINE

A. (1-Methyl-4-piperidinyl)[3-(2-phenylethyl)-2-pyridinyl]methanol

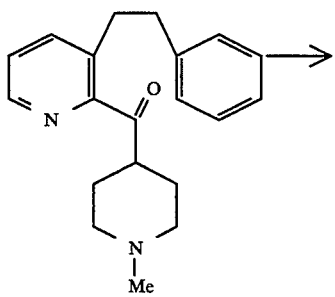

To a mixture of 5.0 g (16.2 mmole) of (1-methyl-4-piperidinyl)[3-(2-phenylethyl)-2-pyridinyl]methanone (which can be prepared in the same manner as described in Preparative Example 1, Steps A–D) in 70 mL of methanol was added portionwise 0.8 g (21.1 mmole) of sodium borohydride. The next day the solution was concentrated in vacuo to give a slurry which was dissolved in water and extracted with CHCl₃. The combined organic portions were dried over MgSO₄, filtered, and concentrated in vacuo to provide a liquid which was distilled (bp 190°–195° C. 1 mm Hg) to give 4.4 gms of the title compound as a viscous oil.

B. 11-(1-Methyl-4-piperidyl)-6,11-dihydro-5H-benzo[5,6]cyclohepta[1,2-b]pyridine

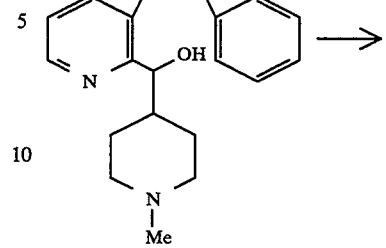

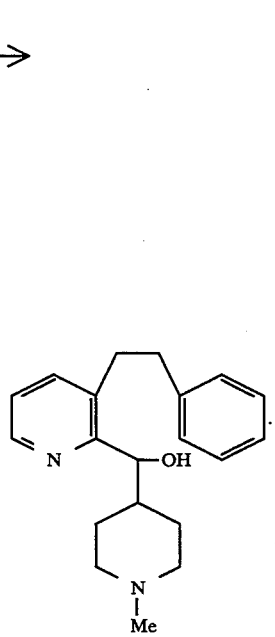

A mixture of 3.5 gm (11.3 mmole) of 4-(1-methyl-piperidyl)-2-[3-(2-phenylethyl)pyridyl]methanol and 200 g of polyphosphoric acid was heated between 160°–170° C. for 13 hours. The mixture was cooled to room temperature, poured into water, basified with aqueous NaOH and extracted with ether. The combined organic portions were concentrated in vacuo and the product recrystallized to give the title compound as a white solid, (mp 111°–114° C.).

C. In a similar manner to that described in Example 1, Steps F–G, 11-(1-methyl-4-piperidyl)-6,11-dihydro-5H-benzo[5,6]cyclohepta[1,2-b]pyridine can be converted to 11-(4-piperidyl)-6,11-dihydro-5H-benzo[5,6]cyclohepta[1,2-b]pyridine.

EXAMPLE 1

8-CHLORO-11-(1-METHOXYACETYL-4-PIPERIDYLIDENE)-6,11-DIHYDRO-5H-BENZO[5,6]CYCLOHEPTA[1,2-b]PYRIDINE

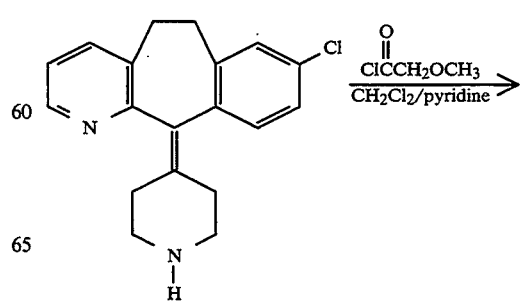

-continued

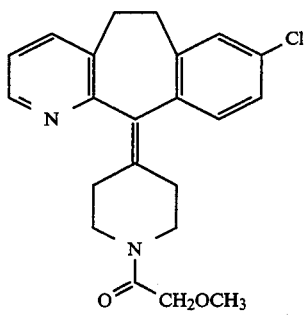

Dissolve the title compound of Preparative Example 1G above, 8-chloro-11-(4-piperidylidene)-6,11-dihydro-5H-benzo[5,6]cyclohepta[1,2-b]pyridine (3.00 gm, 9.7 mmol) and 1.2 mL (14.8 mmol) of pyridine in dry methylene chloride (20 mL) at 0° C. under an argon atmosphere. Add methoxyacetyl chloride (1.1 mL, 12.0 mmol) dropwise, and slowly warm to room temperature. After 1.5 hours take up the mixture in methylene chloride and wash with brine. Dry over $Na_2SO_4$, filter, and concentrate in vacuo to give a residue and purify via flash chromatography. Triturate the product with pentane and recrystallize from ethyl acetate/pentane to give the title compound as a white solid. (1.89 g, m.p. 104°–106° C.).

EXAMPLE 2

8 OR 9-SUBSTITUTED-11-(1-SUBSTITUTED-4-PIPERIDYLIDENE)-6,11-DIHYDRO-5H-BENZO[5,6]CYCLOHEPTA[1,2-b]PYRIDINE COMPOUNDS

By substituting the acid halide and amine listed in the first and second columns, respectively, of Table IV below for the methoxyacetyl chloride and compound of Preparative Example 1G, respectively in the process described in Example 1 above, the product compounds listed in the third column of Table IV were prepared. Workup times were determined by monitoring the reaction by TLC. Reaction times and temperatures vary slightly. In some instances purification of the product by chromatography was not necessary.

TABLE IV

| Acid Halide ClCO—R, R = | $R^3$ | $R^4$ | ($R^3$ and $R^4$ same as in Amine) R = | Z = | Product Melting Point °C. | Comments |
|---|---|---|---|---|---|---|
| —$C_6H_5$ | —Cl | —H | —$C_6H_5$ | O | — | glassy solid |
| —$CH_3$ | —Cl | —H | —$CH_3$ | O | 155–157° C.[a] | |
| —$C(CH_3)_3$ | —Cl | —H | —$C(CH_3)_3$ | O | 158–160° C.[b] | |
| —$CH_2C(CH_3)_3$ | —Cl | —H | —$CH_2C(CH_3)_3$ | O | 137–139° C.[b] | |
| trimethoxyphenyl (OCH₃, OCH₃, OCH₃) | —Cl | —H | trimethoxyphenyl (OCH₃, OCH₃, OCH₃) | O | 178–180° C.[b] | |
| —$CO_2C_2H_5$ | —Cl | —H | —$CO_2C_2H_5$ | O | 126–128° C.[c] | |
| cyclopropyl | —Cl | —H | cyclopropyl | O | 136–138° C. | |
| —$CH_2CH_2CH_3$ | —Cl | —H | —$CH_2CH_2CH_3$ | O | 119–122° C.[d] | |
| —$SC_2H_5$ | —Cl | —H | —$SC_2H_5$ | O | 167.5–168.5° C.[c] | triturated from pentane after flash chromatography |
| —$C_2H_5$ | —Cl | —H | —$C_2H_5$ | O | 128–130° C.[a] | |
| —$CH_2OC_2H_5$ | —Cl | —H | —$CH_2OC_2H_5$ | O | 107–109° C. | triturated from isopropyl ether after flash chromatography |

TABLE IV-continued

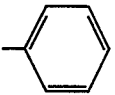 Amine      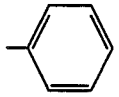 Product

| Acid Halide ClCO—R, R = | R³ | R⁴ | (R³ and R⁴ same as in Amine) R = | Z = | Product Melting Point °C. | Comments |
|---|---|---|---|---|---|---|
| —CH(CH₃)OCH₃ | —Cl | —H | —CH(CH₃)OCH₃ | O | 128–130° C. [c,d] | |
| —C(O)CH₃ | —Cl | —H | —C(O)CH₃ | O | 150–152° C. [c] | |
| —CH₂OCH₃ | —H | —Cl | —CH₂OCH₃ | O | 104–107° C. [c] | |
| —CH₂OCH₃ | —CH₃ | —H | —CH₂OCH₃ | O | — | glassy solid |
| —CH₂OCH₃ | —H | —H | —CH₂OCH₃ | O | 87–89° C. | |
| —CH₂OCH₃ | —F | —H | —CH₂OCH₃ | O | 114–116° C. [c] | |
| —CH₂CH₂CH₃ | —F | —H | —CH₂CH₂CH₃ | O | 123–125° C. [c] | |
| —CH₂OCH₃ | —H | —F | —CH₂OCH₃ | O | 113–115° C. [c] | |
| —CH₃ | —H | —F | —CH₃ | O | — | glassy solid |
| —CH₃ | —F | —H | —CH₃ | O | — | glassy solid |
| —CH₂OCH₃ | —F | —F | —CH₂OCH₃ | O | 151–152° C. [c] | |
| —C(O)CH₃ | —Cl | —H | —CH(OH)CH₃ [e] | O | — | glassy solid |
| —C₆H₅ | —Cl | —H | —C₆H₅ | S | 147–150° C. [f] | [g] |
| —CH₃ | —CH₃ | —H | —CH₃ | O | — | glassy solid |
| —CH₃ | —Cl | —Cl | —CH₃ | O | 177–179° C. | |
| —CH₃ | —Cl | —H | —CH₃ | S | 153–155° C. | [g] |
| —CH₃ | —OCH₃ | —H | —CH₃ | O | — | glassy solid |
| —CH₃ | —H | —Cl | —CH₃ | O | — | glassy solid |
| —CH₃ | —F | —F | —CH₃ | O | 188–189° C. | |
| —CH₃ | —H | —H | —CH₃ | O | 155–156° C. | |
| 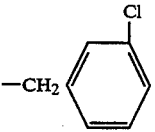 | —H | —H | 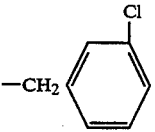 | O | 207–208° C. | |
| 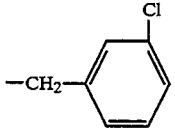 | —H | —H | 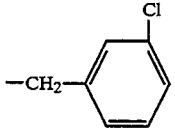 | O | 157–158° C. | |
| 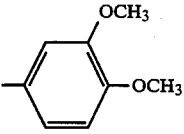 | —H | —H | 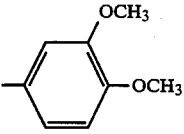 | O | 138–141° C. | |
| —CH₃ | —Br | —H | —CH₃ | O | 165–166° C. | |
| —CH₃ | 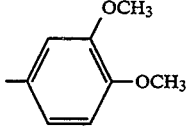 | | —CH₃ | O | 160–162° C. | |
| —CH₂CH=CH₂ | —Cl | —H | —CH₂CH=CH₂ | O | 157–158° C. | |
| C(CH₃)₂OCH₃ | Cl | H | C(CH₃)₂OCH₃ | O | 147–149° C. | |
| —CHCl₂ | Cl | H | CHCl₂ | O | 153–155° C. | |

TABLE IV-continued

| | | | (R³ and R⁴ same as in Amine) | | Product Melting | Comments |
|---|---|---|---|---|---|---|
| Acid Halide ClCO—R, R = | R³ | R⁴ | R = | Z = | Point °C. | |
| —CH₃ | (CH₃) | (Cl) | CH₃ | | — | white glass |
| —CH₃ | (CH₃) | (Cl) | CH₃ | | 103–106° C. | glass |
| —CH₃ | (OH) | (Cl) | (=O) | | — | glass following oxidation with PDC in CH₂Cl₂ |
| —CH₃ | | (Cl) | | | 177–179° C. | |

TABLE IV-continued

| | Amine | | | Product | | | |
|---|---|---|---|---|---|---|---|
| Acid Halide ClCO—R, R = | $R^3$ | $R^4$ | ($R^3$ and $R^4$ same as in Amine) R = | | Z = | Product Melting Point °C. | Comments |
| —CH$_2$OCH$_3$ | | | | | | — | glass |

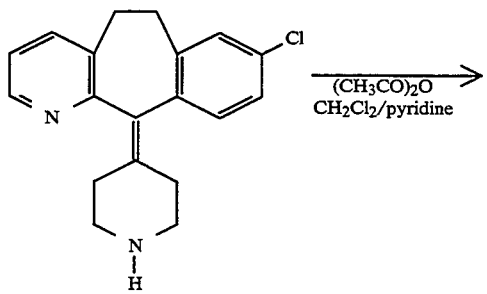

*Recrystallized form acetone and pentane.
[b] Recrystallized from ethylacetate and isopropylether.
[c] Recrystallized from ethylacetate and pentane.
[d] Recrystallized from isopropyl ether.
[e] Following reduction with NaBH$_4$ in methanol.
[f] Recrystallized with ethylacetate and diethylether.
[g] The Z=O compound produced is converted to the Z=S compound by a conventional sulfuration reaction employing Lawesson's reagent.

EXAMPLE 3

8-CHLORO-11-(1-ACETYL-4-PIPERIDYLIDENE)-6,11-DIHYDRO-5H-BENZO[5,6]CYCLOHEPTA[1,2-b]PYRIDINE

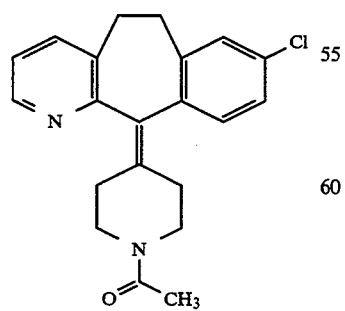

An alternate method of making the title compound is to dissolve the title compound of Preparative Example 1G (3.02 g., 9.72 mmole) and pyridine (3.9 mL, 48.1 mmol) in dry methylene chloride (40 mL) at 0° C. under an argon atmosphere and add dropwise acetic anhydride (4.5 mL, 47.7 mmole). Slowly warm the reaction mixture to room temperature. After 2 hours, take up the mixture in methylene chloride, wash with water (2×) and with brine. Dry the mixture over sodium sulfate, filter and concentrate in vacuo to give a product which is recrystallized from acetone and pentane to give the title compound as a white solid. (2.41 gm, m.p. 155°–157° C.).

EXAMPLE 4

8 OR 9-SUBSTITUTED-11-(1-SUBSTITUTED-4-PIPERIDYLIDENE)-6,11-DIHYDRO-5H-BENZO[5,6]CYCLOHEPTA[1,2-b]PYRIDINE COMPOUNDS

By substituting the acid anhydride and amine listed in the first and second columns, respectively, of Table V below for the acetic anhydride and compound of Preparative Example 1G, respectively in the process described in Example 3 above, the product compounds listed in the third column of Table V were prepared. Workup times were determined by monitoring the reaction by TLC. Reaction times and temperatures vary slightly. In some instances purification of the product by chromatography was not necessary.

TABLE V

| Acid Anhydride O(COR)₂ R = | R³ | R⁴ | R = (R³ and R⁴ same as in Amine) | Z = | Product Melting Point °C. | Comments |
|---|---|---|---|---|---|---|
| —CH₃ | R³ = Cl, R⁵ = H, R⁶ = CH₃, X = N | R⁴ = H | R = CH₃ | Z = O | — | glass |
| —CH₃ | R³ = Cl, R⁵ = R⁶ = CH₃, X = N | R⁴ = H | R = CH₃ | Z = O | — | glass, no pyridine was employed in alkylation |
| —CH₃ | R³ = R⁴ = H, R⁵ = R⁶ = H, X = CH | | R = CH₃ | Z = O | — | glass |
| —CH₃ | (structure) | | | | 112–115° C. | |
| —CF₃ | (structure) | | | | 142–144° C. | |

EXAMPLE 5

8-CHLORO-11-(1-ACETYL-(Z)-2,6-DIMETHYL-4-PIPERIDYLIDENE)-6,11-DIHYDRO-5H-BENZO[5,6]CYCLOHEPTA[1,2-b]PYRIDINE

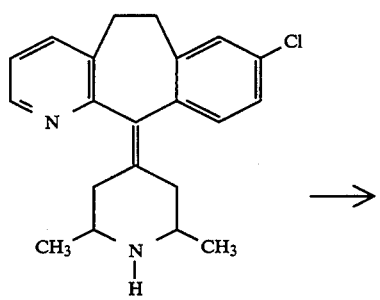

→

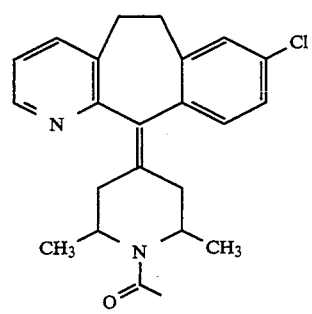

To a solution of 8-chloro-11-(1-acetyl-(Z)-2,6-dimethyl-4-piperidylidene)-6,11-dihydro-5H-benzo[5,6]cyclohepta[1,2-b]pyridine (50 mg, 0.147 mmol) and N,N-dimethylaminopyridine (24 mg, 0.19 mmol) in dry CH₂Cl₂ (2.6 mL) was added acetic anhydride (60 μl, 0.63 mmol). The reaction was stirred for 16 hours. The reaction was quenched with water and then diluted Na₂CO₃ solution. The product was extracted with CH₂Cl₂ and washed with brine, dried (Na₂SO₄), filtered and solvent removed to give a crude product which was isolated from preparative TLC plates (eluted with 5% MeOH in CHCl₃) to give the title compound (42 mg).

By a similar procedure 8-chloro-11-(1-acetyl-(E)-2,6-dimethyl-4-piperidylidene)-6,11-dihydro-5H-benzo[5,6-]cyclohepta[1,2-b]pyridine was prepared.

EXAMPLE 6

8-CHLORO-11-[1-(ETHOXYCARBONYLME-THYL)-4-PIPERIDYLIDENE]-6,11-DIHYDRO-5H-BENZO[5,6]CYCLOHEPTA[1,2-b]PYRIDINE mmol), toluene (20 mL) and tetrahydrofuran (10 mL) at room temperature under an argon atmosphere. Add dropwise ethyl bromoacetate (1.30 mL, 11.7 mmol). After 1.5 hours, filter the mixture and concentrate in vacuo. Purify the residue via flash chromatography. Triturate the product with pentane and recrystallize from isopropyl ether to give the title compound as a white solid. (2.5 gins, Yield 65%, m.p. 80°–82° C.).

EXAMPLE 7

Substitute the appropriate halide and amine from Table VI below into the process of Example 6 to yield the product compounds listed in column 3 of Table VI. The completion time for the reaction is determined by monitoring the reaction by TLC. The reaction time and temperature vary slightly. In some instances purification of the product by chromatography is not necessary.

TABLE VI

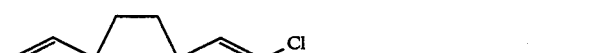

| Halide ClCH₂R R = | Amine | Product | Comments |
|---|---|---|---|
| —CH₂OCH₂CH₂OH | R³ = Cl, R⁴ = H | R³ = Cl, R⁴ = H, Z = H₂<br>R = —CH₂OCH₂CH₂OH | glassy solid[a] |
| 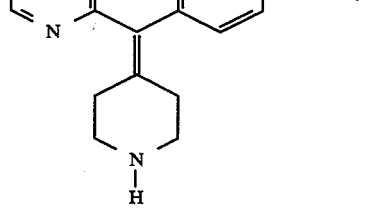 | R³ = Cl, R⁴ = H, | R³ = Cl, R⁴ = H, Z = H₂<br>R = —CH₂CH₂CH(OH)—C₆H₄—C(CH₃)₃ | glassy solid[b] |

[a]Reaction utilizes KI and K₂CO₃ in toluene; Reflux 8 hours.
[b]Obtained by reduction of the precursor ketone with NaBH₄ in methanol.

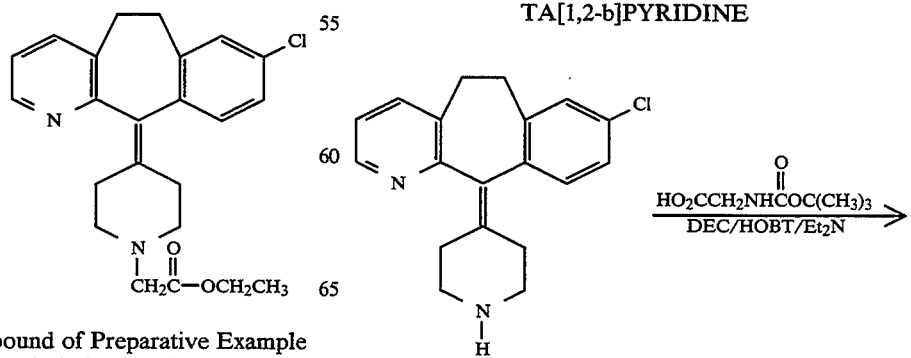

Dissolve the title compound of Preparative Example 1G (3.0 g., 9.7 mmol) in triethylamine (2.0 mL, 14.3

EXAMPLE 8

8-CHLORO-11-[1-(t-BUTOXYCAR-BONYLAMINOACETYL)-4-PIPERIDYLIDENE]-6,11-DIHYDRO-5H-BENZO[5,6]CYCLOHEP-TA[1,2-b]PYRIDINE

-continued

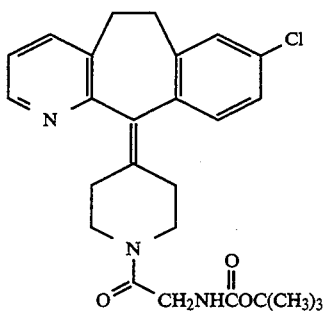

Dissolve N-t-butoxycarbonylglycine (1.84 g, 10.5 mmol), 1-(3-dimethylaminopropyl)-3-ethylcarbodiimide hydrochloride (DEC) (2.80 g, 14.6 mmol), 1-hydroxybenzotriazole hydrate (HOBT) (1.98 g, 14.7 mmol), in triethylamine (Et₃N) (2.0 mL, 14.3 mmol) and dry methylene chloride (30 mL) at 0° C. and under an argon atmosphere. Add dropwise a solution of the title compound from Preparative Example 1G (3.0 g., 9.7 mmol) in dry methylene chloride (15 mL). After 1.5 hours, take up the mixture in methylene chloride and wash with water and then with brine. Dry over sodium sulfate, filter and concentrate in vacuo to give an oil which is purified with flash chromatography (5% MeOH in CHCl₃). Recrystallize the purified product from ethyl acetate and pentane to give the title compound as a white solid. (4.15 gm, m.p. 209°–211° C.).

EXAMPLE 9

8-CHLORO-11-(1-AMINOACETYL-4-PIPERIDYLIDENE)-6,11-DIHYDRO-5H-BEN-ZO[5,6]CYCLOHEPTA[1,2-b]PYRIDINE

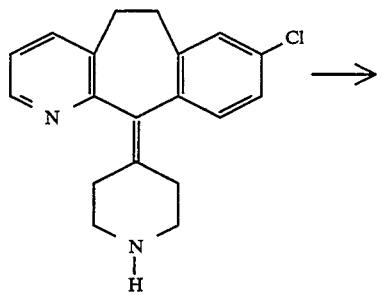

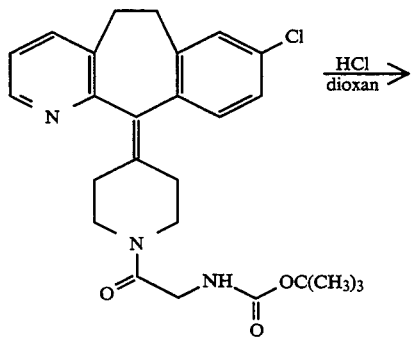

Mix the title compound of Example 8 (2.50 g., 5.34 mmol) in a saturated hydrogen chloride solution in dioxan (35 mL), and stir at room temperature under an argon atmosphere overnight. Concentrate the mixture in vacuo and triturate the resultant gummy product with ethanol and diethylether to give the title compound as white solid. (2.28 g.)

EXAMPLE 10

8-CHLORO-11-(1-FORMYL-4-PIPERIDYLIDENE)-6,11-DIHYDRO-5H-BEN-ZO[5,6]CYCLOHEPTA[1,2-b]PYRIDINE

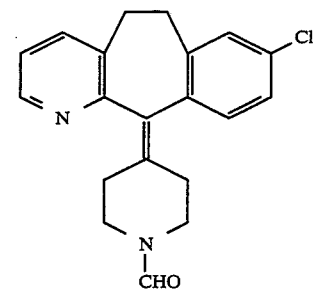

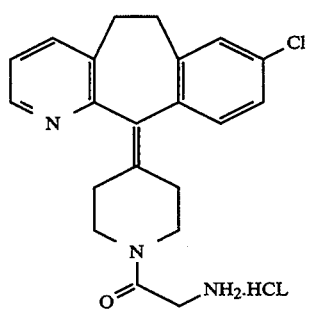

Dissolve the title compound of Preparative Example 1G (5.0 g., 16.1 mmol) in 100 mL of ethyl formate and reflux the mixture for 4 hours. Concentrate the mixture in vacuo and triturate the product with hexane to give the title compound as a white solid (2.2 gm, m.p. 147°–149° C.).

EXAMPLE 11

8-CHLORO-11-(1-METHYLAMINOCARBONYL-4-PIPERIDYLIDENE)-6,11-DIHYDRO-5H-BEN-ZO[5,6]CYCLOHEPTA[1,2-b]PYRIDINE

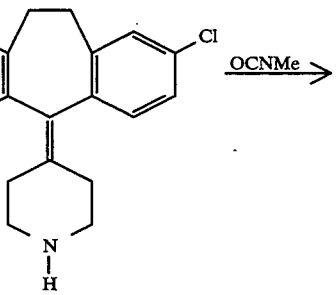

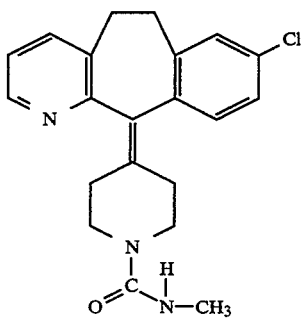

To a mixture of 2.03 g (6.53 mmole) of 8-chloro-11-(1-acetyl-4-piperidylidene)-6,11-dihydro-5H-benzo[5,6]cyclohepta[1,2-b]pyridine and 1.0 mL of triethylamine in 30 mL of dry THF at −10° C. and under a nitrogen atmosphere was added dropwise over 10 minutes 0.40 mL (6.78 mmole) of methylisocyanate. The mixture was slowly warmed to room temperature. After 4 hours it was poured in water and extracted 3× with $CH_2Cl_2$. The organic portions were combined, dried over $MgSO_4$, filtered and concentrated in vacuo to afford a product which was recrystallized from $CH_2Cl_2$/ethyl acetate/hexanes to give 1.70 g of the title compound as white crystals. (m.p. 194.5°–196° C.).

EXAMPLE 12

5-HYDROXY-8-CHLORO-11-(1-ACETYL-4-PIPERIDYLIDENE)-6,11-dihydro-5H-BENZO[5,6-]CYCLOHEPTA[1,2-b]PYRIDINE

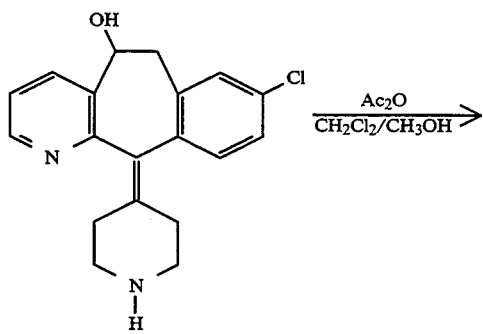

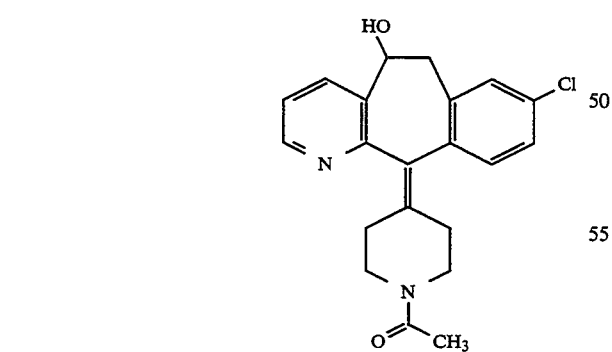

To a mixture of 32.6 mg (0.10 mmole) of 5-hydroxy-8-chloro-11-(4-piperidylidene)-6,11-dihydro-5H-benzo[5,6]cyclohepta[1,2-b]pyridine and 9.7)1 (0.12 mmole) of pyridine in a solution of 2 mL of methanol and 1 mL of $CH_2Cl_2$ at 0° C. and under a nitrogen atmosphere was added 11.3 )1 (0.12 mmole) of acetic anhydride. After 30 min. the mixture was poured into water which was subsequently adjusted to pH of about 9 with aqueous sodium hydroxide. The mixture was extracted 2× with $CH_2Cl_2$. The organic portions were combined, washed once with brine, dried over $Na_2SO_4$, filtered, and concentrated in vacuo to yield 31.2 mg of the title compound as a glass.

EXAMPLE 13

N-METHYL-8-CHLORO-11-(1-ACETYL-4-PIPERIDYLIDENE)-6,11-DIHYDRO-5H-BENZO[5,6]CYCLOHEPTA[1,2-b]PYRIDINIUM IODIDE

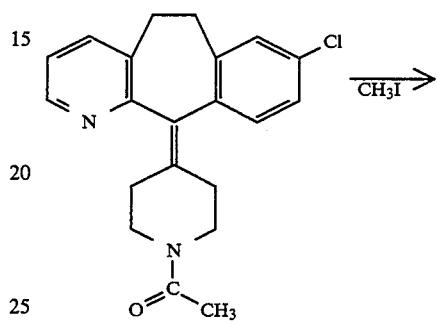

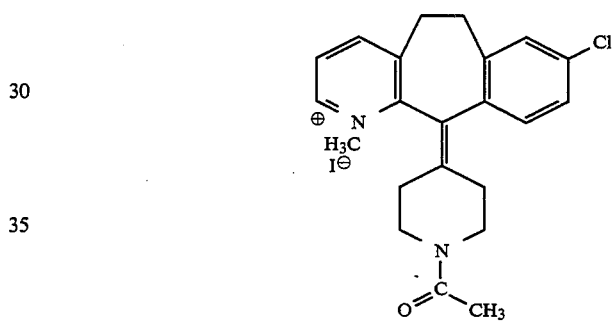

A mixture of 500 mg (1.42 mmole) of 8-chloro-11-(1-acetyl-4-piperidylidene)-6,11-dihydro-5H-benzo[5,6]cyclohepta[1,2-b]pyridine and 175 μl (2.81 mmole) of methyl iodide in 30 mL of toluene was heated at 100° C. for about 19 hours. The reaction mixture was cooled to room temperature and the solvent decanted off. The remaining residue was recrystallized twice from $CH_2Cl_2$/isopropyl ether/hexanes to give 432 mg of the title compound as tan crystals. (m.p. 245°–247° C.).

EXAMPLE 14

8-CHLORO-11-(1-ACETYL-4-PIPERIDYLIDENE)-6,11-DIHYDRO-5H-BENZO[5,6]CYCLOHEPTA[1,2-b]PYRIDINE-N-OXIDE

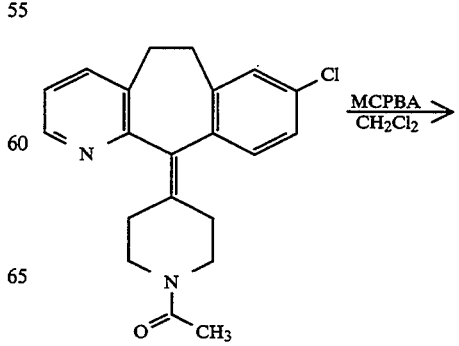

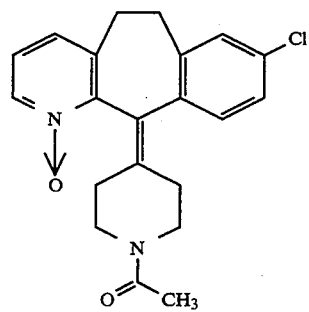

To a mixture of 711 mg (2.01 mmole) of 8-chloro-11-(1-acetyl-4-piperidylidene)-6,11-dihydro-5H-benzo[5,6-]cyclohepta[1,2-b]pyridine in 30 ml of dry $CH_2Cl_2$ at $-10°$ C. and under a nitrogen atmosphere was added 246 mg (1.60 mmole) of m-chloroperoxybenzoic acid. After 95 min. the mixture was taken up in $CH_2Cl_2$ and washed once with 10% aqueous sodium bisulfite and once with 10% aqueous sodium hydroxide. It was dried over magnesium sulfate, filtered, and concentrated in vacuo. The product was purified via flash chromatography (MeOH in $CH_2Cl_2$) and recrystallized from ethyl acetate/hexanes to give 175 mg of the title compound as a hemi-ethyl acetate solid. (m.p. 90.5°–93° C.)

In a similar manner 8,9-difluoro-11-(1-acetyl-4-piperidylidene)-6,11-dihydro-5H-benzo[5,6]cyclohepta[1,2-b]pyridine was converted to 8,9-difluoro-11(1-acetyl-4-piperidylidene)-6,11-dihydro-5H-benzo[5,6]cyclohepta[1,2-b]pyridine-N-oxide.

EXAMPLE 15
8-CHLORO-11-(1-ACETYL-4-PIPERAZINYL)-6,11-DIHYDRO-5H-BENZO[5,6]CYCLOHEPTA[1,2-b]PYRIDINE

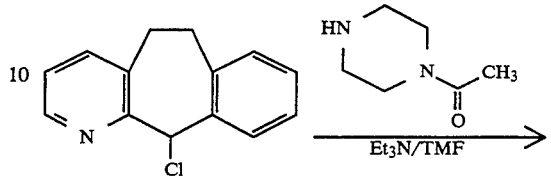

A mixture of 1.98 g (7.50 mmole) of 8,11-dichloro-6,11-dihydro-5H-benzo[5,6]cyclohepta[1,2-b]pyridine, 1.16 g (9.05 mmole) of N-acetylpiperazine, and 2.0 mL of triethylamine in 20 mL of dry THF was refluxed under a nitrogen atmosphere for 16 hr. It was then poured into 5% aqueous sodium hydroxide and extracted three times with methylene chloride. The combined organic portions were dried over $MgSO_4$, filtered and concentrated in vacuo to yield a product which was purified by flash chromatography (5% $CH_3OH$ in $CHCl_3$) to afford 1.71 g of the title compound as a glass.

EXAMPLE 16

By employing the appropriately substituted piperazine listed in Table VII in place of N-acetyl piperazine the desired products were prepared under basically the same conditions as described above. Workup time was determined by TLC.

TABLE VII

Product

| Amine | Product | m.p. | Comments |
|---|---|---|---|
| H-N piperazine-N-CH3 | -N N-CH3 | 146-148° C. | |

TABLE VII-continued

Product

| Amine | Product | m.p. | Comments |
|---|---|---|---|
| (piperazine with 2-CH3, NH) | (N-piperazinyl with CH3, NH) | glass | run at ambient temp, then reflux |
| (piperazine with 2,6-diCH3, NH) | (N-piperazinyl with 2 CH3, NH) | glass | run at ambient temp., then reflux |
| (piperazine, NH) | (N-piperazinyl, NH) | 143–146° C. | employed large excess (11 equiv.) of piperazine with no Et3N run at ambient temp. |
| (bicyclic piperazine with lactam) | (N-bicyclic piperazine with lactam) | glass | piperazine was limiting reagent |

EXAMPLE 17

8-CHLORO-11-[1-ACETYL-4-PIPERIDINYL]-11H-BENZO[5,6]CYCLOHEPTA[1,2-b]PYRIDINE

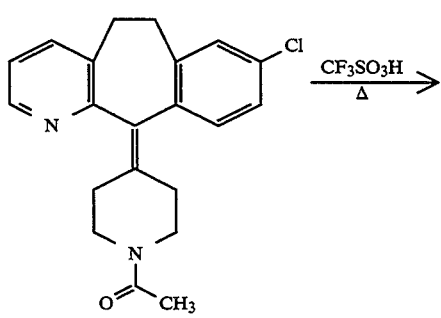

$\xrightarrow{CF_3SO_3H, \Delta}$

-continued

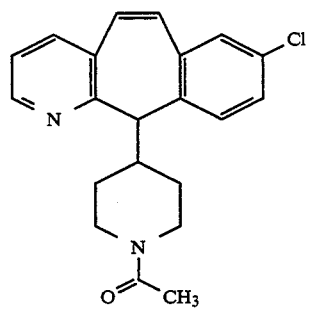

A mixture of 1.17 g (3.32 mmol) of 8-chloro-(1-acetyl-4-piperidylidene)-6,11-dihydro-5H-benzo[5,6]cyclohepta[1,2-b]pyridine in 4 mL of trifluoromethane sulfonic acid was heated between 180°–200° C. for 3 days under a nitrogen atmosphere. The mixture was cooled to room temperature, poured into 10% aqueous sodium hydroxide and extracted three times with CH$_2$Cl$_2$. The organic portions were combined, dried over MgSO$_4$, filtered, and concentrated in vacuo. The residue was purified via flash chromatography [5% MeOH in CH$_2$Cl$_2$] to give 534 mg of the title compound as a glass.

The following are examples of pharmaceutical dosage forms which contain a compound of the invention. As used therein, the term "active compound" is used to designate the compound 8-chloro-11-(1-acetyl-4piperidylidene)-6,11-dihydro-5H-benzo[5,6]cyclohepta[1,2-b]pyridine. The scope of the invention in its pharmaceutical composition aspect is not to be limited by the examples provided, since any other compound of structural formula I can be substituted into the pharmaceutical composition examples.

PHARMACEUTICAL DOSAGE FORM EXAMPLES

EXAMPLE A

| No. | Ingredient | Tablets mg/tablet | mg/tablet |
|---|---|---|---|
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

METHOD OF MANUFACTURE

Mix item nos. 1 and 2 in a suitable mixer for 10–15 minutes. Granulate the mixture with item no. 3. Mill the damp granules through a coarse screen (e.g., ¼") if needed. Dry the damp granules. Screen the dried granules if needed and mix with item no. 4 and mix for 10–15 minutes. Add item no. 5 and mix for 1–3 minutes. Compress the mixture to appropriate size and weight on a suitable tablet machine.

EXAMPLE B

| No. | Ingredient | Capsules mg/capsule | mg/capsule |
|---|---|---|---|
| 1. | Active Compound | 100 | 500 |
| 2. | Lactose USP | 106 | 123 |
| 3. | Corn Starch, Food Grade, | 40 | 70 |
| 4. | Magnesium Stearate NF | 4 | 7 |
|   | Total | 250 | 700 |

METHOD OF MANUFACTURE

Mix item nos. 1, 2 and 3 in a suitable blender for 10–15 minutes. Add item no. 4 and mix for 1–3 minutes. Fill the mixture into suitable two-piece hard gelatin capsules on a suitable encapsulating machine.

While the present invention has been described in connection with certain specific embodiments thereof, it will be evident to one of ordinary skill in the art that many alternatives, modifications and variations may be made. All such alternatives, modifications and variations are intended to be included within the spirit and scope of the invention.

We claim:

1. A compound having the name:
1-(4-pyridinylcarbonyl)-4-(8-chloro-5,6-dihydro-11H-benzo[5,6]cyclohepta-[1,2-b]pyridin-11-ylidene)-piperidine,i.e.,

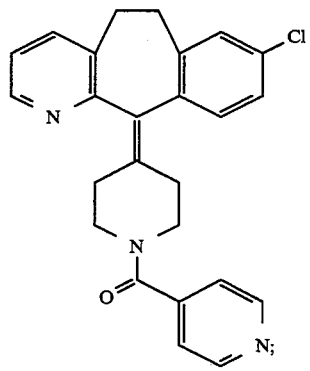

1-(2-pyridinylcarbonyl)-4-(8-chloro-5,6-dihydro-11H-benzo[5,6]cyclohepta-[1,2-b]pyridin-11-ylidene)-piperidine;
1-(3-pyridinylcarbonyl)-4-(8-chloro-5,6-dihydro-11H-benzo[5,6]cyclohepta-[1,2-b]pyridin-11-ylidene)-piperidine;
1-(2-pyrazinylcarbonyl)-4-(8-chloro-5,6-dihydro-11H-benzo[5,6]cyclohepta[1,2-b]pyridin-11-ylidene)-piperidine; or
1-(4-pyridazinylcarbonyl)-4-(8-chloro-5,6-dihydro-11H-benzo[5,6]cyclohepta[1,2-b]pyridin-11-ylidene)-piperidine.

2. A pharmaceutical composition comprising a compound as defined in claim 1 in combination with a pharmaceutically acceptable carrier.

3. A method of treating allergy comprising administering a compound as defined in claim 1 to a mammal in need of such treatment in an amount effective to treat allergy.

4. A method of treating inflammation comprising administering to a mammal in need of such treatment an antiinflammatory effective amount of a compound as defined in claim 1.

5. A compound having the name:
1-(4-pyridinylcarbonyl)-4-(8-chloro-5,6-dihydro-11H-benzo[5,6]cyclohepta-[1,2-b]pyridin-11-ylidene)-piperidine, i.e.,

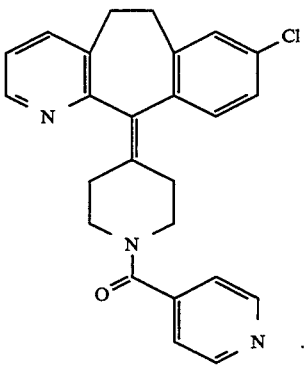

6. A pharmaceutical composition comprising a compound as defined in claim 5 in combination with a pharmaceutically acceptable carrier.

7. A method of treating allergy comprising administering a compound as defined in claim 5 to a mammal in need of such treatment in an amount effective to treat allergy.

8. A method of treating inflammation comprising administering to a mammal in need of such treatment an antiinflammatory effective amount of a compound as defined in claim 5.

* * * * *